United States Patent
Nibbering et al.

(10) Patent No.: US 6,884,776 B1
(45) Date of Patent: Apr. 26, 2005

(54) ANTIMICROBIAL PEPTIDES DERIVED FROM UBIQUICIDINE

(75) Inventors: Petrus Hendricus Nibbering, Voorhout (NL); Pieter Sicco Hiemstra, Leiderdorp (NL); Maria Theodora Van Den Barselaar, Wassenaar (NL); Ernest Karel Jacob Pauwels, Leiden (NL); Rolf Ide Johannes Feitsma, Leiden (NL)

(73) Assignee: RijksUniversiteit Leiden (NL)

( * ) Notice: Subject to any disclaimer, the term of this patent is extended or adjusted under 35 U.S.C. 154(b) by 0 days.

(21) Appl. No.: 09/424,815

(22) PCT Filed: May 18, 1998

(86) PCT No.: PCT/NL98/00311

§ 371 (c)(1),
(2), (4) Date: Apr. 10, 2000

(87) PCT Pub. No.: WO98/54314

PCT Pub. Date: Dec. 3, 1998

(30) Foreign Application Priority Data

May 29, 1997 (NL) .............................................. 1006164

(51) Int. Cl.$^7$ ............................................... A61K 38/00
(52) U.S. Cl. .......................................................... 514/12
(58) Field of Search ........................... 514/12; 530/300

(56) References Cited

U.S. PATENT DOCUMENTS 6,319,503 B1 * 11/2001 Kenten et al. ........... 424/192.1

FOREIGN PATENT DOCUMENTS

| JP | 08176193 | * | 7/1996 |
| JP | 08176193 A | * | 7/1996 |

OTHER PUBLICATIONS

English translation of JP 08176193 A.*
Olvera J, Wool IG. The carboxyl extension of a ubiquitin–like protein is rat ribosomal protein S30. J Biol Chem. Aug. 25, 1993;268(24):17967–74.*
XP–00205805, Nelson, Christopher A., et al., "Identification of the naturally processed form of hen egg white lysozyme bound to the murine major histocompatibility complex class II molecule I–A", Proc. Nat'l Acad Sci. USA, vol. 89 pp. 7380–7383, Aug. 1992, Immunology.
XP–002052804, Kas, Koen et al., "Genomic structure and expression of the human fau Gene: encoding the ribosmal protein S30 fused to a ubiquitin–like protein", Biochemical and Biophysical Research Communications, vol. 187, No. 2, 1992, pp. 927–933.
Hiemstra, Pieter S., et al., "Antimicrobial Proteins of Murise Macrophages", Infection and Immunity, vol. 61, No. 7. Jul. 1993, pp. 3038–3046.

(Continued)

Primary Examiner—Karen Cochrane Carlson
Assistant Examiner—Sheridan K Snedden
(74) Attorney, Agent, or Firm—Webb Ziesenheim Logsdon Orkin & Hanson, P.C.

(57) ABSTRACT

The invention relates to the use of ubiquicidine or optionally modified peptide fragments derived therefrom for the preparation of a drug for the treatment, diagnostics or prophylaxis of infections in humans and animals. A peptide fragment derived from ubiquicidine comprises for instance a preferably continuous series of at least 3, preferably at least 7–13 amino acids from the amino acid sequence of ubiquicidine; K V H G S L A R A G K V R G Q T P K V A K Q E K K K K K-TGRAKRRMQYNRRFVNVVPTFGKKKGPN ANS (SEQ ID NO: 1). Hybrid molecules comprise for instance a cationic peptide with an antimicrobial action and/or a peptide fragment of ubiquicidine and/or a derivative thereof and one or more effector molecules.

16 Claims, 17 Drawing Sheets

OTHER PUBLICATIONS

Pauwels, E.K.J. et al., "The Labeling of Proteins and LDL wish", Tc: a New Direct Method Employing KBH$_4$ and Stammous Chlorida, Nucl. Med. Biol., vol. 20, No. 7 pp. 823–833, 1993.

XP–002052807, Malcherek, Georg et al., "Natural peptide ligand motifs of two HLA molecules associated with myasthenia gravis", Chemical Abstracts, vol. 120.

XP–002052808, Miyazaki, Toshiuki et al., "Basic proteins derived from wheat germs for treatment . . . ", Chemical Abstracts, vol. 118.

de Kosser, H. Saskis et al., "The use of dedicated peptide libraries permits the discovery of high affinity binding peptides", Journal of Immunological Methods, vol. 187, (1995) pp. 179–188.

Martin, Edith et al., "Defensins and other esdogenous peptide antibiotics of vertebrates", Journal of Leukocyte Biology, vol. 58, Aug. 1995, pp. 128–136.

XP–002052806, Ridgway, William M. et al., "Breaking self–tolerance in nonobese diabetic mice", Chemical Abstracts, vol. 124.

* cited by examiner

| PEPTIDE | | |
|---|---|---|
| Ubiquicidine: (59aa, 6.654 kD) | KVHGSLARAGKVRGQTPKVAKQEKKKKKTGRAKRRMQYNRRFVNVVPTFGKKKGPNANS (SEQ ID NO: 1) | |
| (1-18, 2.153 kD) | KVHGSLARAGKVRGQTPK | (SEQ ID NO: 2) |
| (29-41, 1.910 kD) | TGRAKRRMQYNRR | (SEQ ID NO: 3) |
| (18-29, 1.643 kD) | KVAKQEKKKKKT | (SEQ ID NO: 4) |
| (18-35, 3.477 kD) | KVAKQEKKKKKTGRAKRR | (SEQ ID NO: 5) |
| (18-35, 3.656 kD) | AKVAKQEKKKKKTGRAKRRA | (SEQ ID NO: 6) |
| (29-35, 953 D) | TGRAKRR | (SEQ ID NO: 7) |
| (42-59, 2.213 kD) | FVNVVPTFGKKKGPNANS | (SEQ ID NO: 8) |
| (36-41, 957 D) | MQYNRR | (SEQ ID NO: 9) |

FIG. 1

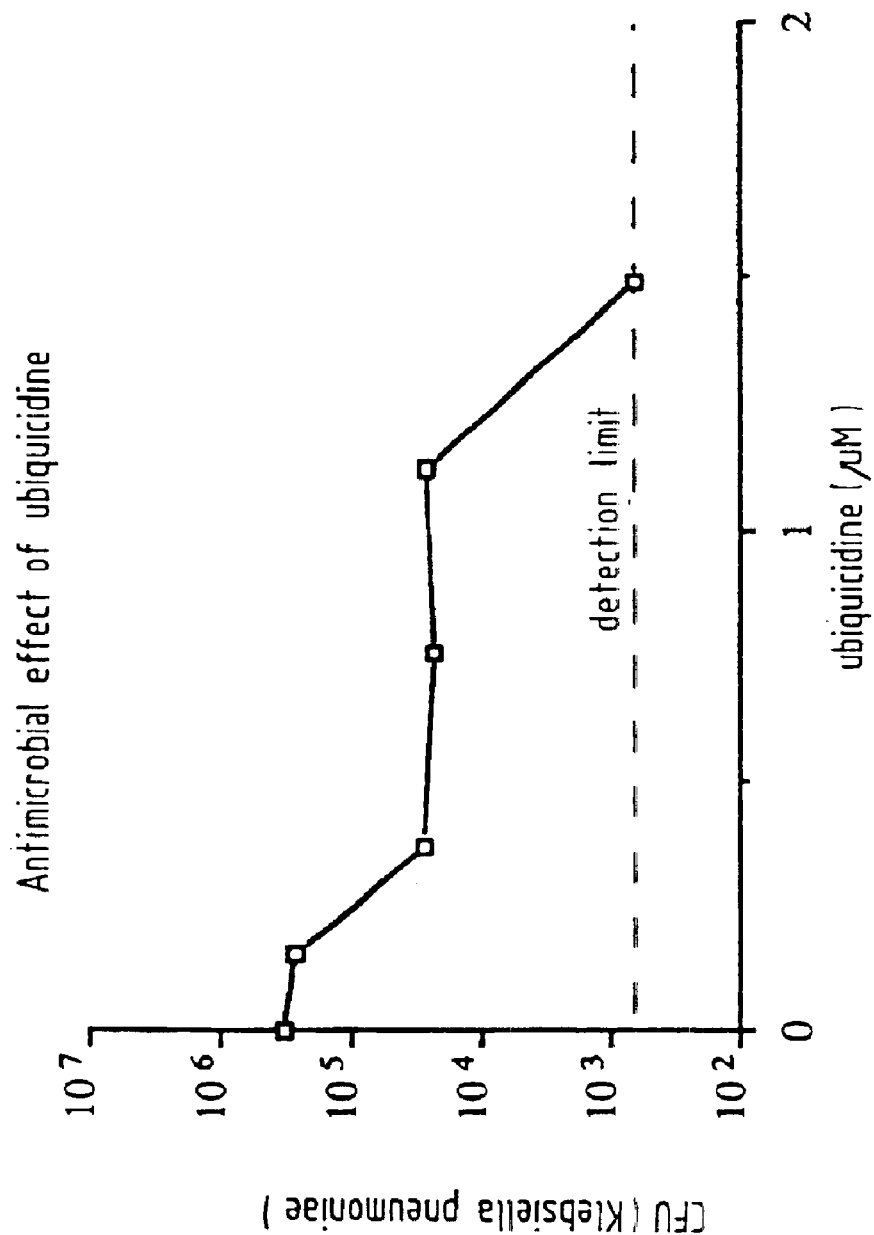

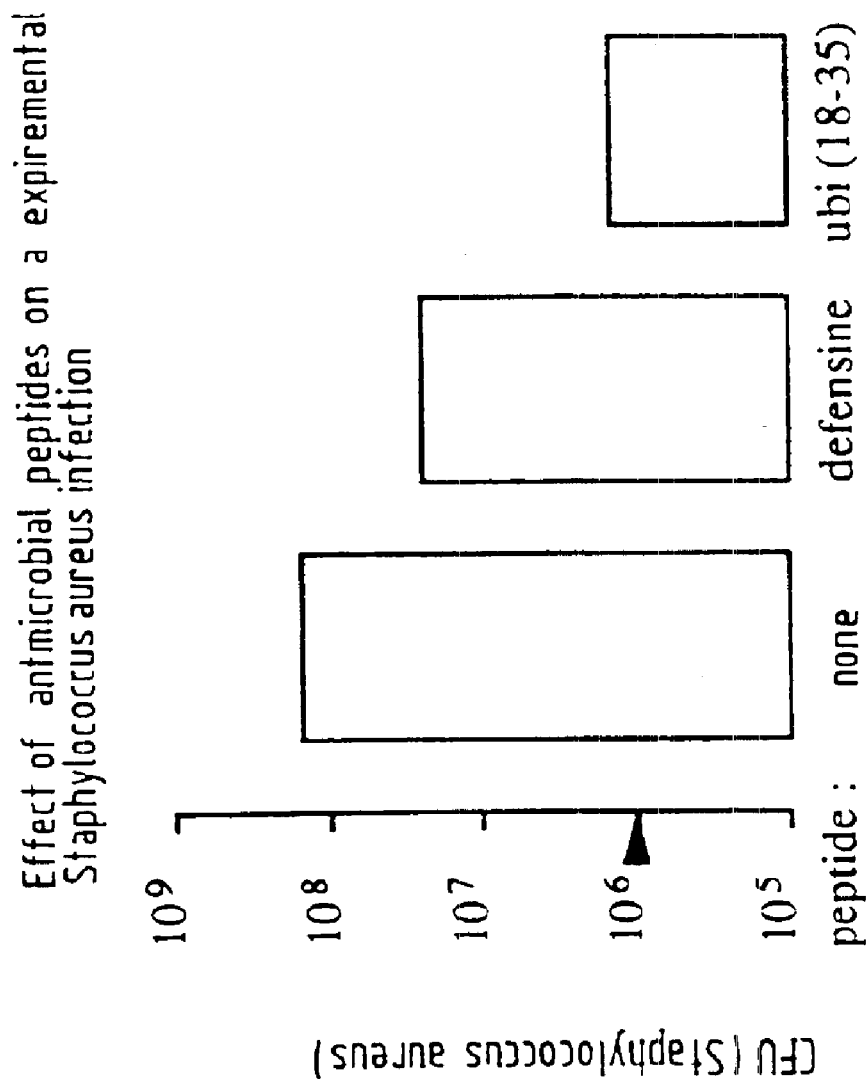

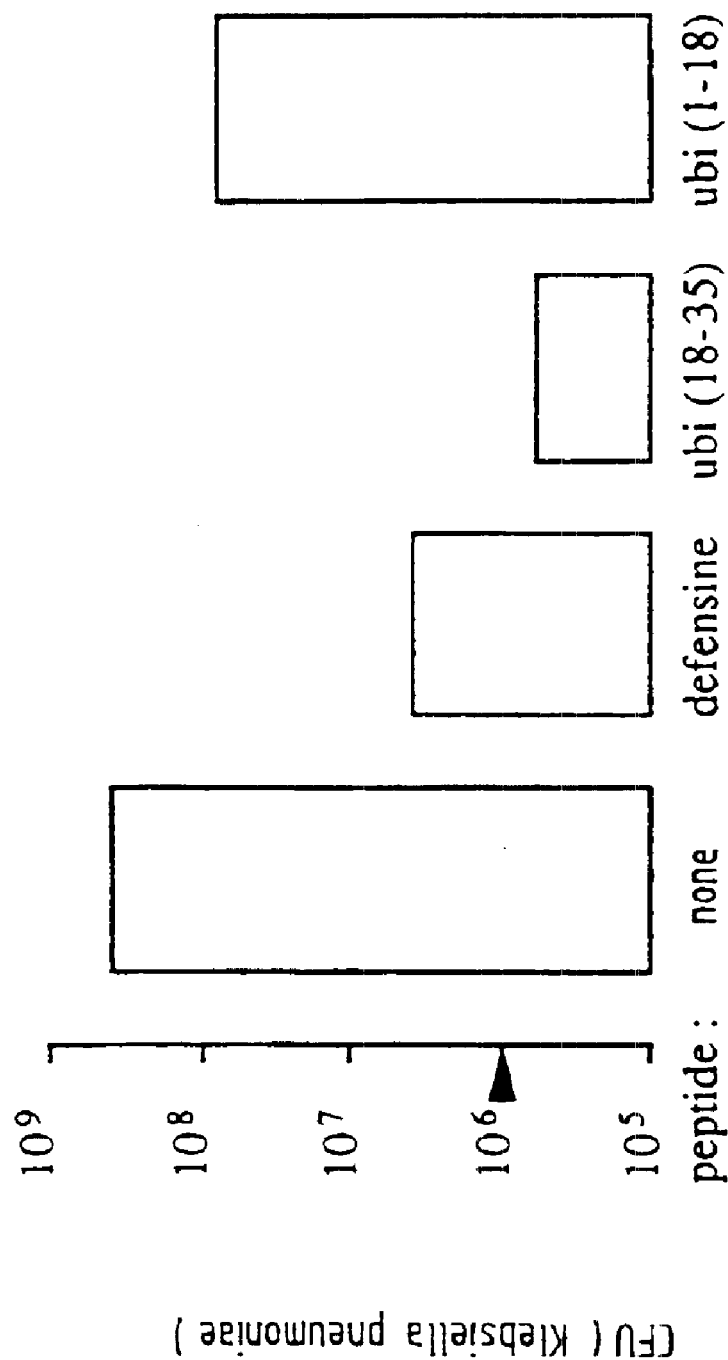

Antimicrobial effect of ubiquidine 29-41 and 18-35 and defensin-1 in mouses
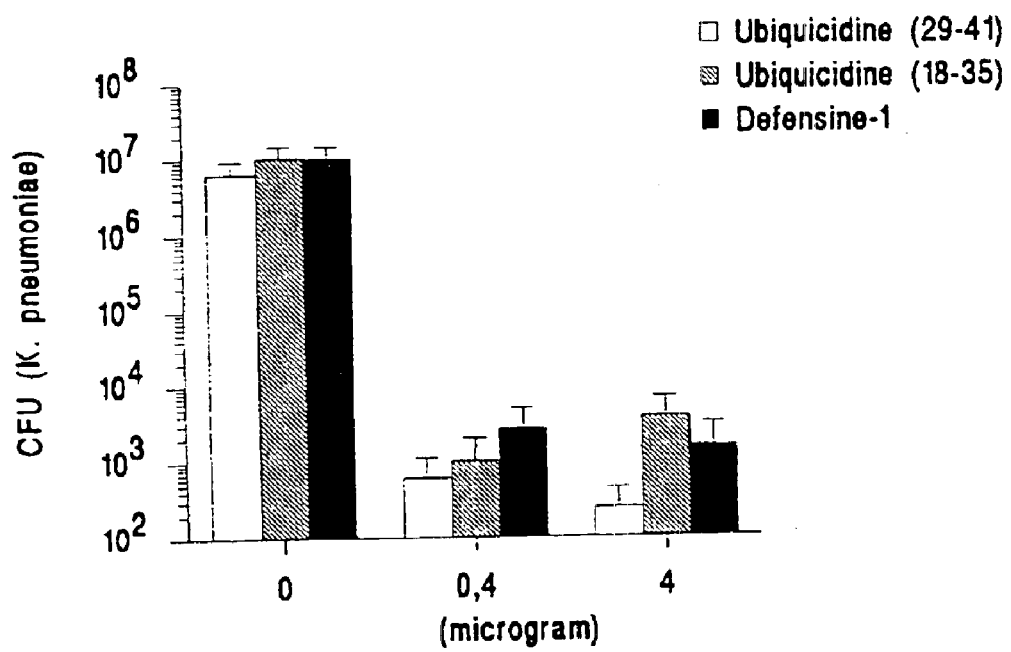
Antimicrobial effect of ubiquidine 29-41 and 18-35 and defensin-1 in mouses treated with cyclofosfamide
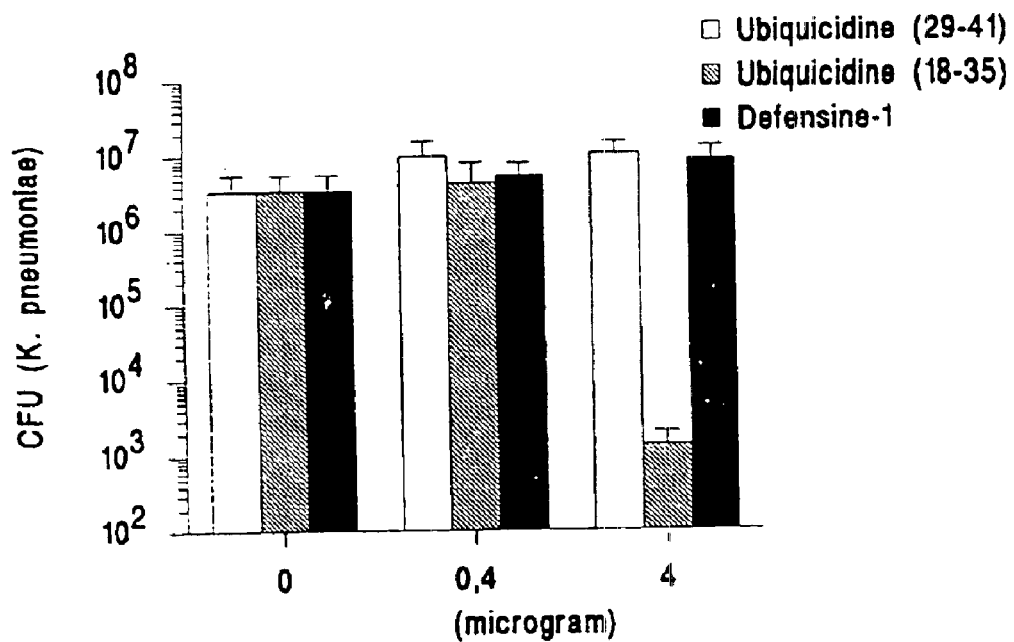
FIG.15

ANTIMICROBIAL PEPTIDES DERIVED FROM UBIQUICIDINE

The present invention relates to the new medical use of a per se known peptide, which will be referred to as "ubiquicidine" in this application. The invention further relates to new peptide fragments derived from this peptide, optionally in modified form or provided with a (radioactive) label, and the use hereof in prophylaxis, therapy and diagnostics of infections in humans and animals. The invention also relates to new antimicrobial and diagnostic agents on the basis of the peptide, the peptide fragments and/or modified versions thereof, optionally in the form of combination preparations. Finally, the invention also provides a new method for preparing radioactively labelled peptides with antimicrobial activity.

In an increasing number of cases the use of what are called "classic" antibiotics is not sufficient for the treatment of infectious diseases. Many bacteria strains have built up resistance against the known classes of antibiotic and in the last thirty years no new classes of antibiotic have been discovered. There are few or no adequate agents against mycobacteria. And other micro-organisms, such as fungi, and determined parasites are also sometimes difficult to treat with existing antimicrobial agents. In view of the above, a new class of antimicrobial agents is highly desirable.

At present, two new types of antimicrobial agents are attracting attention. On the one hand there are the carbohydrate-type agents. In addition, research is focussing on peptides, particularly (cationic) peptides, with antimicrobial activity. Cationic peptides contain a relatively large number of positively charged amino acids, such as arginine and lysine, and therefore carry a net positive charge, usually of at least +2, but often +4 or more. Antimicrobial peptides are an important component of the natural defence of most living organisms against infections. Many such antimicrobial peptides are cationic. In humans and other mammals such peptides, such as the defensins, are an important protein-like constituent of for instance neutrophil granulocytes. These cells are already involved at a very early stage in the defence against micro-organisms and in acute inflammation reactions. In addition, such peptides are also produced by many other cells, including epithelial cells, which are strategically located in relation to invading micro-organisms.

In the research which resulted in the present invention, it was found that the per se known peptide FAU S30 (which has now been called "ubiquicidine" by the present inventors) has antimicrobial action. It was further found that peptide (fragments) derived from this peptide also have an antimicrobial action to a lesser or greater extent. These peptide (fragments) as such have not been described previously and are therefore still new.

On the basis of this conclusion, the present invention provides the use of ubiquicidine or optionally modified peptide (fragments) derived therefrom for preparing a drug for the treatment, diagnostics or prophylaxis of infections in humans and animals.

The advantage of ubiquicidine and fragments thereof is that they not only have an antimicrobial and immunomodulating action, but that they also make their way in the body in targeted manner to the actual site of infection and accumulate there. These peptide (fragments) are therefore infection-seeking.

In this application "antimicrobial action" is understood to mean any inhibiting or otherwise negative effect on bacteria, viruses, protozoa, parasites and fungi.

"Immunomodulating action" is understood in this application to mean any stimulating effect on body cells of humans and/or animals involved in the defence against infections.

"Ubiquicidine" is understood in this application to mean a peptide of 6.654 kD with an amino acid sequence as shown in FIG. 1.

Peptide fragments derived from ubiquicidine comprise a preferably continuous series of at least 3, preferably at least 8 amino acids from the amino acid sequence of ubiquicidine as shown in FIG. 1. For an average skilled person it is simple to ascertain whether a peptide fragment with a series of preferably continuous amino acids chosen from the amino acid sequence of ubiquicidine does actually have antimicrobial activity and thus meets the requirements of the invention. A simple standard test for determining antimicrobial activity is for instance the universally known growth-killing test, i.e. determining of the concentration of an antimicrobial agent which kills 99% of the micro-organisms (IC 99%). Designated by "peptide (fragments)" in this application are therefore all amino acid chains which are smaller than the ubiquicidine itself, but the amino acid sequence of which is to be found, preferably continuously, in the ubiquicidine. The length of such peptide (fragments) can vary from 3 to 58 amino acids, wherein possible extra amino acids added as modification are not included.

Examples of peptide (fragments) are the peptides of which the sequence is shown in FIG. 1. Ubiquicidine (18–35)-D-alanine has as extra addition a D-alanine at both ends. Of the peptide fragments shown in FIG. 1, ubiquicidine (1–18), ubiquicidine (18–35) and ubiquicidine (29–41) are particularly recommended. In the above described test the activity of these fragments lies around 1 $\mu$M. This is a particularly good antimicrobial activity. In principle however, all the above defined peptides, which display some inhibiting action or other on micro-organisms, fall within the invention. Peptides with an IC 99% of a maximum of 25 $\mu$M, preferably a maximum of 10 $\mu$M, most preferably a maximum of 1 $\mu$M are however recommended.

In order to modify their activity, for instance to further increase it, or to inhibit or prevent degradation by enzymes, particularly peptidases, both the peptide (ubiquicidine) and the fragments can be modified in different ways. Modification is any variation from the naturally occurring amino acid chain. Modifications may be mutual linking in reverse sequence of at least a part of the amino acids of the peptide or a peptide fragment. When all amino acids of a peptide (fragment) are thus reversed, this is referred to as "reverse peptide (fragment)".

One or more of the amino acids from the original peptide (fragment) can also be replaced by a stereoisomer of that amino acid. The L-isomers of amino acids occur in the body. The D-stereoisomers can be degraded much less easily by enzymes present in the body and bacterial enzymes. Such a modification ensures that the peptide (fragment) in the body remains intact longer and can exert its effect longer. A similar modification consists of extending the original amino acid chain at one or both ends with one or more groups protecting against degradation, such as D-amino acids, for instance D-alanine.

All the amino acid chains modified in the above described manner or varying in other manner from the corresponding native peptide (fragment) will be designated in this application with the term "derivative". These can be derivatives of the ubiquicidine as well as of fragments thereof.

The invention further relates to so-called "hybrid molecules", which comprise a (cationic) peptide with an antimicrobial action and/or a peptide fragment and/or a derivative thereof according to the invention together with one or more effector molecules. The effector molecule can assume different forms, such as an amino acid chain, which is capable of binding to a micro-organism and/or substances secreted by micro-organisms or expressed on the surface thereof. An example of such an effector molecule is an endotoxin-binding peptide.

Another type of effector molecule can consist of a virus protein. Such a virus protein/antimicrobial peptide can enter the host cell, in which the micro-organism for combatting is situated, in the known manner of a virus and the peptide can exert its antimicrobial action therein.

The effector molecule can further be a detectable label, such as a radionuclide, chosen from the group consisting of technetium 99m (Tc-99m), iodine 123(I-123) and 131 (I-131), bromine 75 (B-75) and 76(B-76), lead 203 (Pb-203), gallium 67 (Ga-67) and 68 (Ga-68), arsenic 72 (As-72), indium 111 (In-111), 113m (In-113m) and 114m (In-114m), ruthenium 97 (Ru-97), copper 62 (Cu-62), 64 (Cu-64) and 67 (Cu-67), iron 52 (Fe-52), manganese 52m (Mn-52m), chromium 51 (Cr-51), rhenium 186 (Re-186) and 188 (Re-188), terbium 161 (Tb-161) and yttrium 90 (Y-90). The radionuclide (also called "emitter") can also fulfil a curative function. Paramagnetic labels, such as fluorine 19 (F-19), sodium 23 (Na-23), phosphorus 31 (P-31), gadolinium 157 (Gd-157), manganese 55 (Mn-55), dysprosium 162 (Dy-162), chromium 52 (Cr-52) and iron 56 (Fe-56) can also be used.

According to the invention combinations of effector molecules can likewise be linked to the peptide. An example thereof are a cell-binding peptide and an emitter, wherein the cell-binding peptide and the antimicrobial peptide provide targeting of the hybrid molecule to the site of infection and the antimicrobial peptide and the emitter provide for treatment or diagnosis.

Hybrid molecules of this type which consist of an antimicrobial peptide, peptide fragment or derivative thereof and at least one effector molecule have not been described previously. The "hybrid molecules" according to the invention are not therefore limited to the ubiquicidine as antimicrobial peptide, but generally comprise hybrid molecules comprising a (cationic) peptide with antimicrobial activity and/or fragments and/or derivatives thereof. Examples of other such antimicrobial peptides are α- and β-defensins, protegrins, serprocidins, magainins, PR-39, cecropins and others (Martin et al. (1995) J. Leukocyte Biol. 58:128–136).

The invention relates to the variants of the peptide or fragments thereof comprehensively described above. These variants as well as the peptide and the fragments can also be designated collectively in this application as "peptide (fragments)".

The invention further relates to an antimicrobial agent comprising as active component ubiquicidine and/or peptide fragments thereof, derivatives of one of both and/or hybrid molecules containing at least ubiquicidine or other antimicrobial cationic peptides and/or peptide fragments thereof and/or derivatives thereof for use in the diagnostics, prophylaxis, monitoring or therapy of infections.

The antimicrobial agent according to the invention can contain only the active component or take the form of a pharmaceutical composition in which one or more other carriers, diluents and the like are present. The agent and the composition can have different forms of administration, such as for instance tablet, pill, capsule, injection, infusion, suppository, powder, suspension, solution, spray, emulsion, ointment, aerosol, plaster or cream and can be used for oral, anal, nasal, vaginal, intramuscular, subcutaneous, intravenous, intraperitoneal or local (topical) administration or administration by means of a catheter via natural or artificial body openings. Other very specific examples of forms of administration are toothpaste, tooth varnish and catheters coated with the active compound. These latter have a prophylactic action.

Compositions according to the invention can be prepared by combining (i.e. mixing, dissolving et cetera) of the active component(s) with pharmaceutically and pharmacologically acceptable excipients with a neutral character (such as aqueous or non-aqueous solvents, stabilizers, emulsifiers, detergents, additives)., and further, where necessary, colorants, aromatic substances and/or flavourings. The concentration of the active component(s) in a pharmaceutical composition can vary between 0.001% and 100% (w/v), depending on the nature of the treatment and the manner of administering. The dose for administering likewise depends on the manner of administration and nature of the treatment. For the mouse for instance a dose of 1 to 10 µg/kg, for instance 4 µg/kg body weight, is suitable. The compositions according to the invention are suitable for treatment of both humans and animals.

The invention further relates to the ubiquicidine, to peptide fragments thereof, to derivatives of one of both and to hybrid molecules containing at least ubiquicidine or other antimicrobial cationic peptides, and/or peptide fragments thereof and/or derivatives thereof for use in diagnostics, prophylaxis, therapy or monitoring of infections.

Infections, which can be treated with the agent are for instance disorders caused by pathogenic Gram-positive (*Staphylococcus aureus, Listeria monocytogenes* including antibiotic-resistant strains of *S. aureus* (also called Multidrug-Resistant *S. aureus* (MRSA))), and Gram-negative ((antibiotic-resistant) *Klebsiella pneumoniae, Escherichia coli*, enterococci and *Salmonella typhimurium*) bacteria, micro-organisms difficult to treat such as *Mycobacterium avium* and *Mycobacterium fortuitum*, fungi such as *Candida albicans, Cryptococcus neoformans* and *Aspergillus fumigatis*, viruses, in particular enveloped viruses, and parasites, such as *Trypanosoma cruzi* and *Toxoplasma gondii*. The use of the agent is however not limited to the infections stated here.

Because the peptide (fragment) according to the invention is infection-seeking, it can be applied very well in the diagnostics of infections and pathology related thereto. If provided with a detectable label, for instance a radioactive label such as technetium 99m, it is possible for instance by means of scintigraphy to determine some time after administering where in the body the peptide (fragment) is situated. This will also be the site where the infection for treatment is situated. Such a labelled peptide (fragment) therefore has a dual purpose. Not only is demonstrated where the infection is situated, but the peptide (fragment) will also exert an antibiotic action due to its presence at the site and thus reduce the infection. In this manner the effect of the treatment can also be followed by looking at the localization of the peptide in time. This is called "monitoring".

Each of the above mentioned radionuclides can in principle be used. Particularly recommended however is technetium 99m ($^{99m}$Tc). The physical half-life of this radionuclide amounts to 6 hours and, together with the fact that particularly gamma radiation is emitted, this means a low radiation load for the patient. The relatively short half-life moreover has the clinical advantage that the examination can be repeated rapidly. In addition, this radionuclide is readily obtainable via the commercially available Mo-Tc-nuclide-generator.

It is found that peptide (fragments) labelled with technetium 99m can already be detected after 15 minutes at the site of the infection. The accumulation of for instance gallium 67 takes at least 24 hours. Owing to the very rapid localization of peptide (fragments) labelled with technetium 99m, a rapid diagnosis is possible. Furthermore, technetium 99m is mainly a γ emitter with a very small quantity of the much more harmful β radiation, so there is a relatively low radiation load for the patient. A more frequent administration is hereby possible. In addition, it has also been found that labelling r with technetium 99m has no adverse influence on the action of the peptide (fragment). In laboratory animal experiments no adverse effects or changed external characteristics due to $^{99m}$Tc-labelled peptide (fragments) have been found up to the present. In vitro studies have moreover shown that very high concentrations of the antimicrobial peptide (fragments) are not toxic for human body cells. Particular recommended therefore according to the invention as hybrid molecules are technetium 99m-labelled cationic peptides and fragments or derivatives thereof.

The peptide (fragments) according to the present invention demonstrate the infection itself and thus the location where the micro-organism is situated in the body. Known image-forming methods for detecting infections, such as X-ray, echography and the like-are aimed at demonstrating morphological changes which are the result of an infection. It is very well possible however for the infection itself to have already disappeared, while the morphological change still exists. In that case the treatment of the infection with for instance antibiotics is simply continued while this is in fact no longer necessary. It is recommended in principle to cause a treatment with a determined antimicrobial agent to be as short as possible in respect of the occurrence of resistances or allergies as a result of the agent. The peptide (fragments) according to the invention are infection-seeking and therefore make their way to the site of the infection itself and can also be made visible there. As soon as the infection has disappeared, this is shown by the fact that the peptide (fragment) no longer accumulates at the site of the (former) infection. The treatment can then be stopped. Using labelled peptides, infections can also be distinguished from inflammation processes. Infections occur when the body reacts to the presence of a foreign living organism. "Inflammation" is a general name for reactions of the body to foreign stimuli, such as particles, molecules, but also live bacteria. The peptide only reacts in the case of infections.

The invention further relates to combination preparations which, in addition to ubiquicidine and/or a peptide fragment thereof and/or a derivative thereof and/or a hybrid molecule, contain one or more other active components. Combinations with "classic" antibiotics or with antiviral or antifungal agents can for instance be envisaged.

The invention further relates to a method for labelling antimicrobial peptides, particularly cationic peptides, more particularly ubiquicidine and peptides derived therefrom and defensins. Such a method comprises of placing the peptide for labelling in contact with a tin(II) salt, a borohydride and a radioactive label in the presence of alkali, as described in Pauwels et al. (Nucl. Med. Biol. 20, 825–833 (1993)), but wherein the peptide is modified with MAG3 (mercaptoacetyl glycine-glycine-glycine). Prior to labelling the modified peptide is held at about 100° C. for 10 minutes. Particularly in the case of small peptides or peptides carrying no sulphur groups, the MAG3 modification results in considerably higher labelling efficiencies.

The whole is stirred at a suitable temperature for a determined time, for instance 1 to 60 minutes, preferably 5 to 30 minutes. The temperature depends on the temperature sensitivity of the peptide, but will usually lie between room temperature and 40° C., and will preferably be about 37° C.

The tin(II) salt is preferably tin(II)pyrophosphate. The borohydride is preferably sodium borohydride or potassium borohydride. The tin(II) salt and the borohydride are advantageously used in a ratio between 1:1 and 1:10, preferably 1:4 in quantities of respectively 0.5–5 µl and 2–10 µl. In preference 0.1 M sodium hydroxide is used as alkali.

The radioactive label is advantageously $^{99m}$Tc-pertechnetate, but $^{186}$Re-perrhenate can also be used. Standard solutions of such radioactive labels are commercially available. In the method according to the invention 0.05–0.5 ml, preferably 0.1 ml of such a solution is used.

A particularly advantageous manner of preparing ubiquicidine, and optionally the fragments, derivatives and hybrid molecules, is by means of transgenic animals. For this purpose the method comprises of transforming an animal egg-cell with a gene construct which codes for the ubiquicidine, peptide fragment, derivative or hybrid molecule, regenerating a transgenic animal from the transformed egg-cell and isolating the ubiquicidine, peptide fragment, derivative or hybrid molecule from a tissue or bodily fluid of the animal, for instance milk. The products can of course also be synthesized.

The present invention will further be elucidated on the basis of the accompanying examples, which are only given by way of illustration but do not limit the invention. Reference is made in the examples to the following figures, in which:

FIG. 1 shows the amino acid sequence of ubiquicidine and derived peptides

FIG. 14 shows the effect of ubiquicidine (18–35), ubiquicidine (1–18) and defensins on an experimental infection with *Staphylococcus aureus* and *Escherichia coli*

FIG. 15 shows the antimicrobial effect of ubiquicidine 29–41 and 18–35 and defensin-1 in mice.

EXAMPLES

Figure 2B:
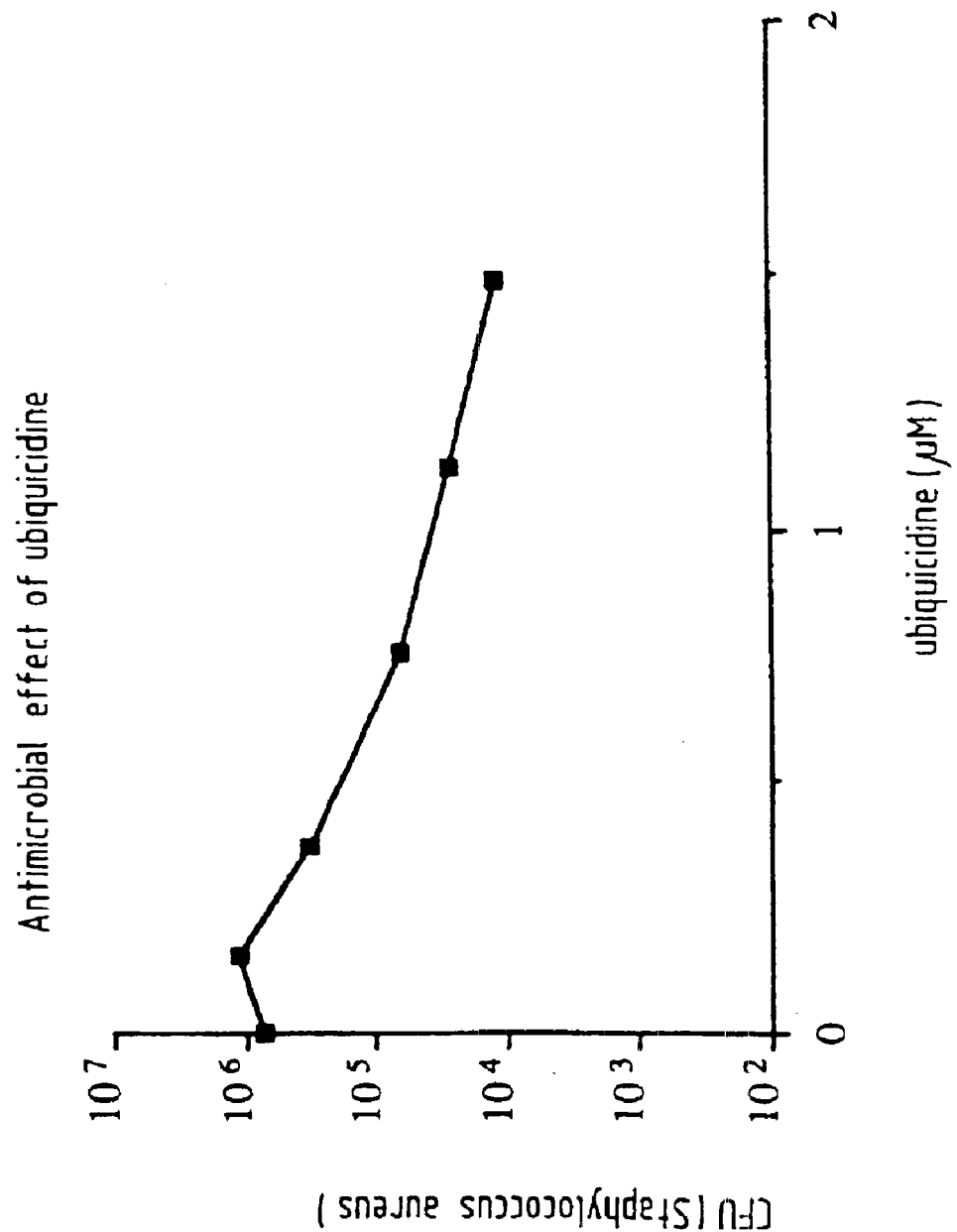
FIG. 2 shows the antimicrobial effect of ubiquicidine in respect of *Klebsiella pneumoniae* and *Staphylococcus aureus*

Example 1
Antimicrobial Action of Ubiquicidine

1. Introduction

By means of gel filtration and reverse phase HPLC a peptide was isolated from the cytosol fraction of murine RAW 264.7 macrophages activated with interferon γ and cells of the human H292 bronchial epithelial cell line stimulated in different ways. The latter could be stimulated with bacterial products (endotoxin, lipoteichoinic acid), phorbol ester, and bronchial pathogens (*Haemophilus influenzae, Streptococcus pneumoniae* and para-influenza virus 3). The isolated peptide was called ubiquicidine.

2. Materials and Method 2.1. Isolation of Ubiquicidine

The method of isolating ubiquicidine from cytosol fractions of cells has been previously described for the isolation of antimicrobial proteins from cell lysates and cell membrane fractions (Hiemstra et al. (1993) Infect Immun. 61:3038–3046). The cells were cultured in RPMI 1640 medium with antibiotics and 10% heat-inactivated foetal calf serum. The cells were subsequently harvested, washed and resuspended in 10 mM sodium phosphate buffer (pH 7.4) enriched with a cocktail of protease inhibitors:

Using nitrogen cavitation, a cell lysate was obtained whereafter by means of ultracentrifugation at 27,000×g a membrane fraction and a cytosol fraction were obtained. The proteins in the cytosol fraction were extracted using 5% acetic acid and the acid extract was dialyzed and subsequently placed on a P60 column.

The fractions originating from this column were tested for antimicrobial activity. The ubiquicidine-containing fractions were pooled and further separated by means of HPLC on a C18 column with heptafluorobutyric acid as "ion pairing molecule" in the eluent. The HPLC fractions were likewise tested for antimicrobial activity and immunoreactivity using an antiserum against the N-terminal part of the ubiquicidine. The pooled fractions contain pure ubiquicidine.

2.2. Biochemical Characterization

The sequence of the N-terminal amino acids of purified ubiquicidine was determined by means of automated Edman degradation and a peptide sequencer 477A equipped with a PTH amino acid analyzer 120A (Applied Biosystems, Foster City, Calif.). The sequence results were subsequently analysed using the GeneWorks software package (Intelligenetics, Mountain View, Calif.). Molecular weight of ubiquicidine was determined using mass spectrometry (laser desorption time-of-flight mass spectrometry; Lasermat, Finnigan MAT LTD, Hemel Hempstead, UK). For the immunological identification of ubiquicidine use was made of a rabbit antiserum specific to the N-terminal part of ubiquicidine (ubiquicidine 1–18) and Western blotting.

2.3. Tests for Antimicrobial Activity In Vitro

Different techniques were used to test for the antimicrobial activity of ubiquicidine and peptides derived therefrom. The gel overlay assay and the radial diffusion assay have been previously described (Hiemstra et al. (Infect. Immun. 63, 3038–3046 (1993)). In the growth-killing curve determination which was used to investigate the IC 99% of the peptide, (mid-log or stationary phase) bacteria (*Klebsiella pneumoniae* (A) and *Staphylococcus aureus* (B) were exposed for 60 minutes at 37° C. to increasing concentrations of the ubiquicidine, whereafter the number of living bacteria in the suspension was determined using microbiological plate techniques (Colony Forming Units, CFU). As negative controls, bacteria were exposed to peptide 4 (a synthetic peptide derived from HIV glycoprotein 120), ubiquicidine (18–29) or no peptide.

The results of such experiments are shown in CFUs in FIG. 2.

3. Result

The ubiquicidine is a 6.7 kD ribosomal cationic peptide with a pI of 12.67. From sequence determination of the 18 N-terminal amino acids of the isolated peptide, it was found that these corresponded wholly with the N-terminal part of the S30 part of the expression product of the Finkel-Biskis-Reilly murine sarcoma associated ubiquitously expressed (FAU) gene which occurs inter alia in humans and mice. The molecular weight of the FAU S30 and the ubiquicidine were also found to correspond. It is therefore assumed that it is the same peptide.

From the determination of the in vitro antimicrobial action of ubiquicidine it was found that the ubiquicidine can kill micro-organisms very rapidly (<10 minutes) and effectively (3–4 log reduction). FIG. 2 shows mid-log *Klebsiella pneumoniae* (A) and *Staphylococcus aureaus* (B), which were exposed for 60 minutes at 37° C. to increasing concentrations of purified ubiquicidine in 10 mM sodium phosphate buffer. In the control incubations the bacteria multiplied a number of times (not shown). The minimal inhibiting concentration for said micro-organisms was found to lie between 0.08 and 0.16 μM, 1.5 μM ubiquicidine eliminates *Klebsiella pneumoniae* (A) almost completely, while the reduction in the number of *Staphylococcus aureus* (B) amounts to 2 log.

Example 2
Antimicrobial Action of Peptide Fragments

1. Introduction

A number of peptide fragments were derived from the native ubiquicidine and the antimicrobial activity thereof was determined.

2. Materials and Methods 2.1. Production of Synthetic Peptides

Peptides were prepared using an Abimed AMS multiple peptide synthesizer and a fixed phase (tentagel AC, a polymer of polyethylene glycol spacer linked to a polystyrene matrix) (de Koster et al. (1995) J. Immunol. Methods 187:179–188). After completion of the synthesis the peptide was released from the fixed phase using a trifluoroacetic acid water(19:1) mixture and the peptides were subsequently precipitated with an ether pentane(1:1) mixture at 20° C. After centrifugation the obtained pep-tides were dried at 40° C. for 15 minutes. The peptides were subsequently dissolved in 10% acetic acid and concentrated by means of vacuum centrifugation. The purity of the peptides was determined using HPLC. An overview of the synthesized peptides derived from ubiquicidine is given in FIG. 1. The antimicrobial activity of these peptide fragments was determined as described in Example 1 under 2.3.

2.2. Antimicrobial Effect on Herpes Simplex Virus (HSV)

Figure 3:
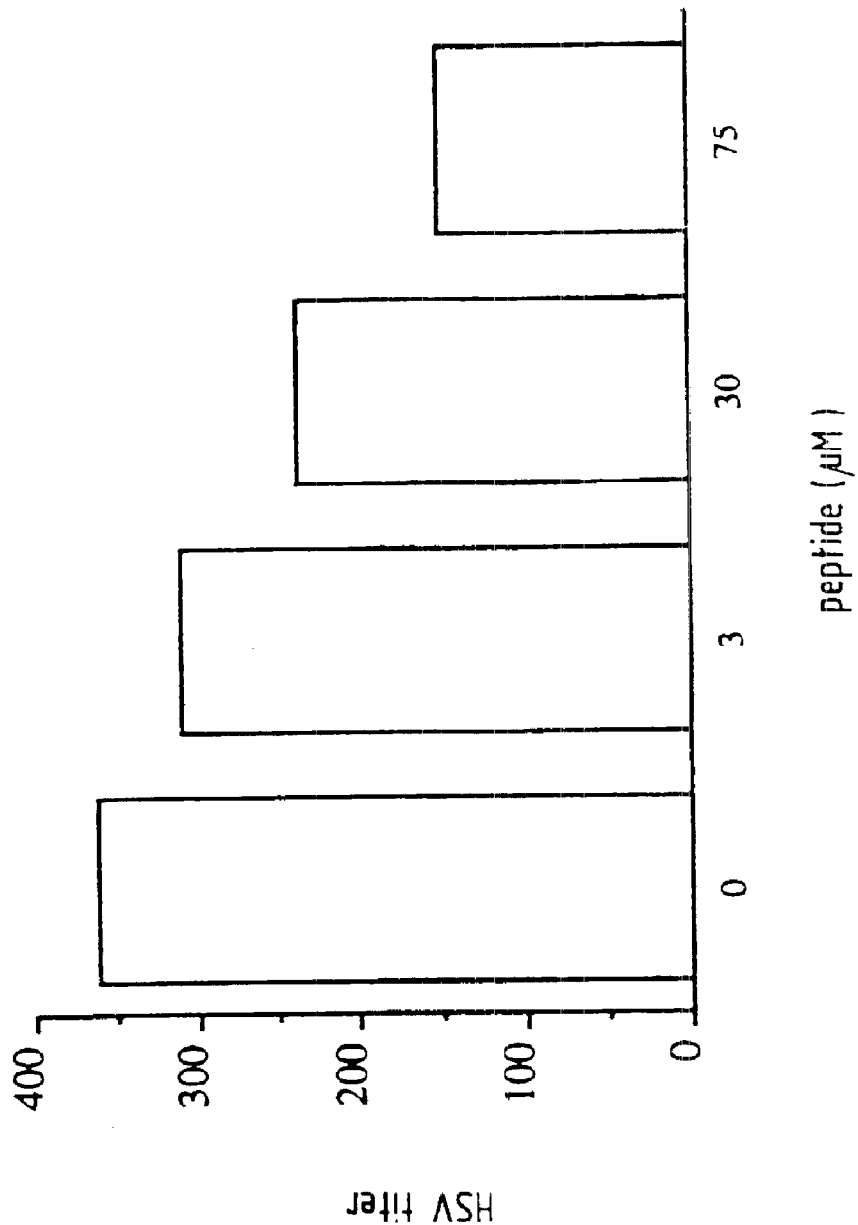
FIG. 3 shows the effect of ubiquicidine (18–35) on herpes simplex virus infection of Vero cells

HSV was incubated for 60 minutes with increasing concentrations of the peptide fragment ubiquicidine (18–35) at 37° C. The virus preparation was subsequently added to Vero cells in diverse dilutions. After 3 days at 37° C. the cytopathogenic effect of the virus on Vero cells was determined, with finally made it possible for the virus titre to be calculated. FIG. 3 shows the result.

2.3. Antimicrobial Effect on *Mycobacterium Fortuitum*

Figure 4:
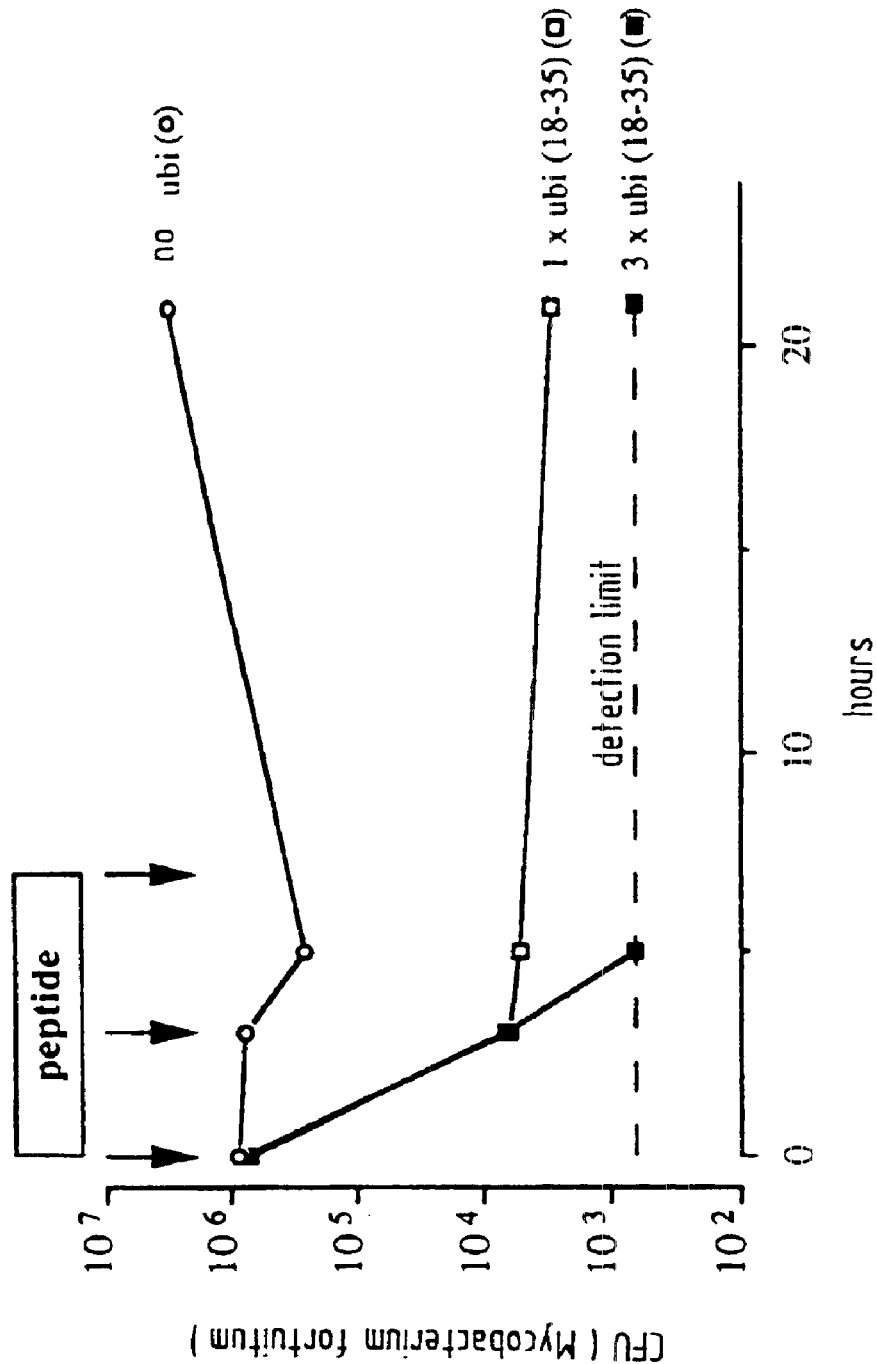
FIG. 4 shows the effect of ubiquicidine (18–35) on *Mycobacterium fortuitum*

About $10^6$ *Mycobacterium fortuitum* were incubated for different intervals at 37° C. with 14 μM or 52 μM ubiquicidine (18–35) and the number of living mycobacteria in the suspensions was then determined using microbiological techniques. The result is shown in FIG. 4.

2.4. Antimicrobial Effect on *Staphylococcus Aureus*

Figure 5:
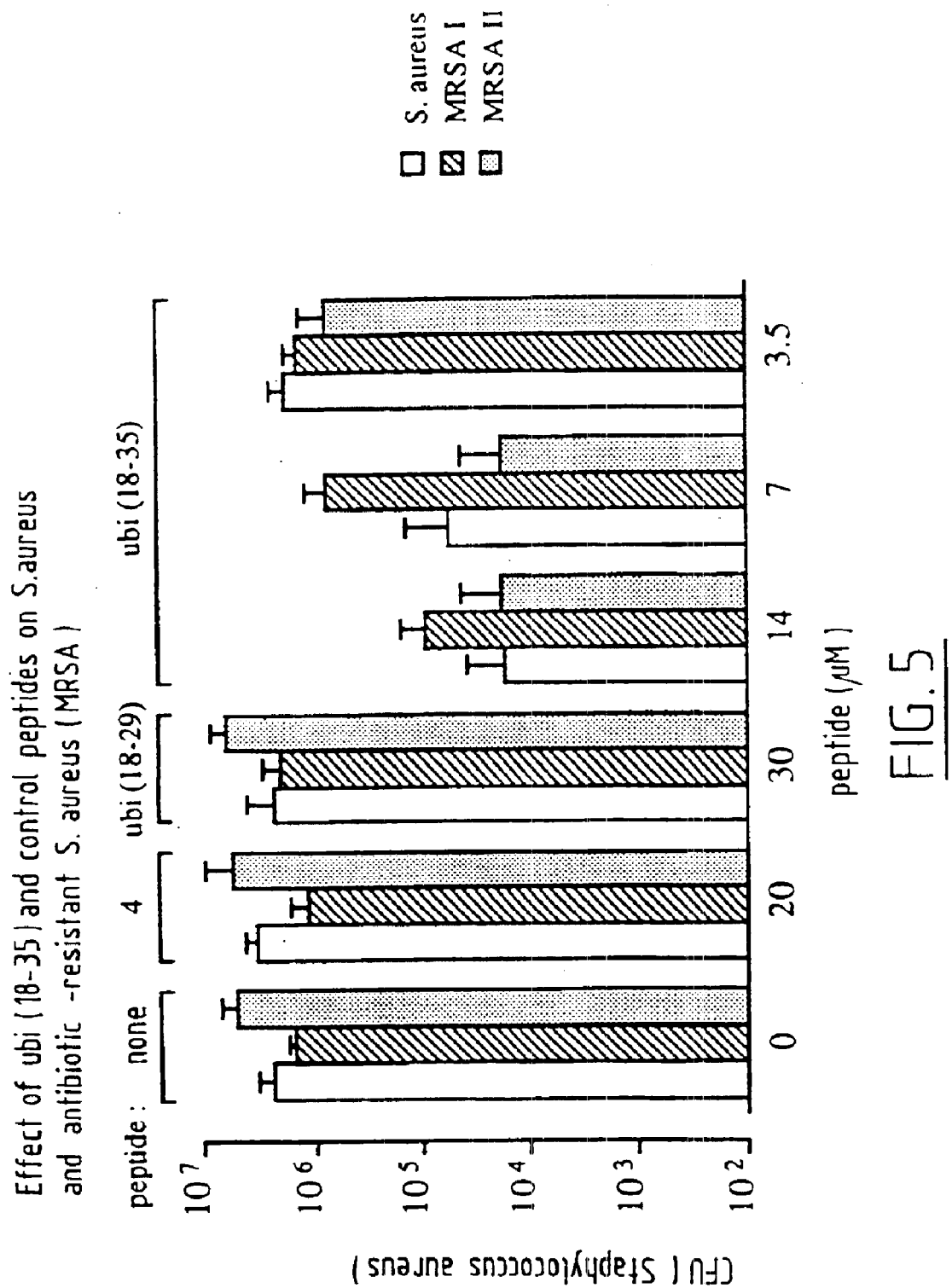
FIG. 5 shows the effect of ubiquicidine (18–35) and ubiquicidine (18–29) on (antibiotic-resistant) *Staphylococcus aureus*

About 10⁶ bacteria of multidrug resistant *Staphylococcus aureus* (MRSA) and antibiotic-sensitive *S. aureus* were exposed for 60 minutes at 37° C. to different concentrations of ubiquicidine (18–35), whereafter the number of living bacteria in the suspensions was determined microbiologically. As negative control high concentrations of ubiquicidine (18–29), peptide 4 and no peptide were used. The result is shown in FIG. 5.

3. Results

Research into the effect of the different peptides on *Klebsiella pneumoniae* and *Staphylococcus aureus* demonstrated antimicrobial activity of ubiquicidine (1–18), ubiquicidine (18–35) and ubiquicidine (29–41). The other peptides were found to be considerably less potent or inactive.

FIG. 3 shows the results of the experiment with HSV. This shows that an increasing concentration of peptide results in a decrease in the virus titre.

FIG. 4 shows that ubiquicidine (18–35) kills *M. fortuitum* for a period of 3 hours, whereafter the peptide then shows a bacteriostatic effect. Repeated administration at 3 and 7 hours after the first dose results in practically complete elimination of the mycobacteria. In the control incubations *M. fortuitum* was found to proliferate. In additional control experiments no indication was found for agglomeration of the mycobacteria due to ubiquicidine (18–35) (not shown).

FIG. 5 shows that the peptide fragment ubiquicidine (18–35) results in a marked decrease in the number of CFUs of different *Staphylococcus aureus* strains.

Example 3
Modified Peptide Fragments and their Activity

1. Introduction

A number of the peptide (fragments) described in Example 2 was further modified in different ways by adding an extra D-alanine at the beginning and/or end as protection against exopeptidase activity. The antimicrobial activity of several "derivatives" obtained in this manner was likewise determined.

2. Materials and Methods 2.1. Production Of Modified Peptides

D-alanine-protected peptides were prepared as described above (Example 2, ad 2.1) in this application.

2.2. Antimicrobial Effect on *Staphylococcus Aureus*

*Staphylococcus aureus* (5×10⁵ bacteria) was exposed for different periods at 37° C. to 7 $\mu$M ubiquicidine (18–35) and D-alanine-protected ubiquicidine (18–35), whereafter the number of living bacteria in the suspension was quantified microbiologically.

In addition, different strains of (multidrug resistant) *Staphylococcus aureus* were incubated for 60 minutes at 37° C. with increasing concentrations of D-alanine-protected and unprotected ubiquicidine (18–35), whereafter the number of living bacteria in the different suspensions was determined microbiologically.

2.3. Antimicrobial Effect on *Klebsiella Pneumoniae*

About 5×10⁶ *Klebsiella pneumoniae* were exposed for 60 minutes at 37° C. to increasing concentrations of ubiquicidine (18–35) and D-alanine-protected ubiquicidine (18–35) and the number of live bacteria was subsequently measured microbiologically.

2.4. Antimicrobial Effect on *Escherichia Coli*

About 10⁶ antibiotic-resistant *Escherichia coli* and antibiotic-sensitive *E. coli* (parent strain of the resistant bacteria) were exposed for 60 minutes at 37° C. to increasing concentrations of D-alanine-protected ubiquicidine (18–35), whereafter the number of living bacteria was determined microbiologically.

3. Results

Figure 6:
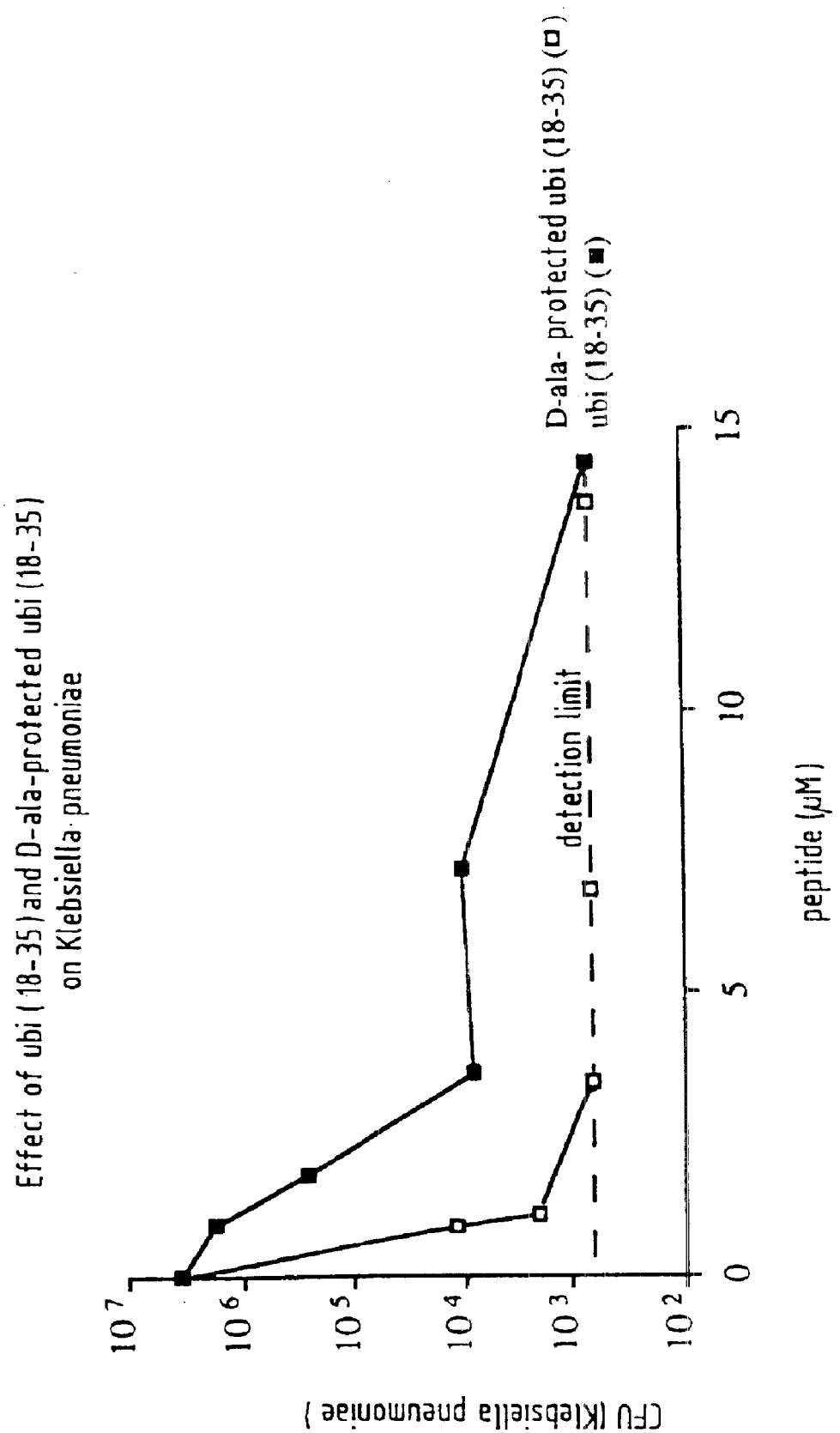
FIG. 6 shows the effect of ubiquicidine (18–35) and D-alanine-protected ubiquicidine (18–35) on *Klebsiella pneumoniae*

Comparison of antimicrobial activities of the D-alanine-protected and the unprotected ubiquicidine (18–35) in respect of *Klebsiella pneumoniae* in vitro showed that the D-alanine-protected variant is much more potent in eliminating the bacteria than the unprotected ubiquicidine (18–35) peptide (FIG. 6).

Figure 7:
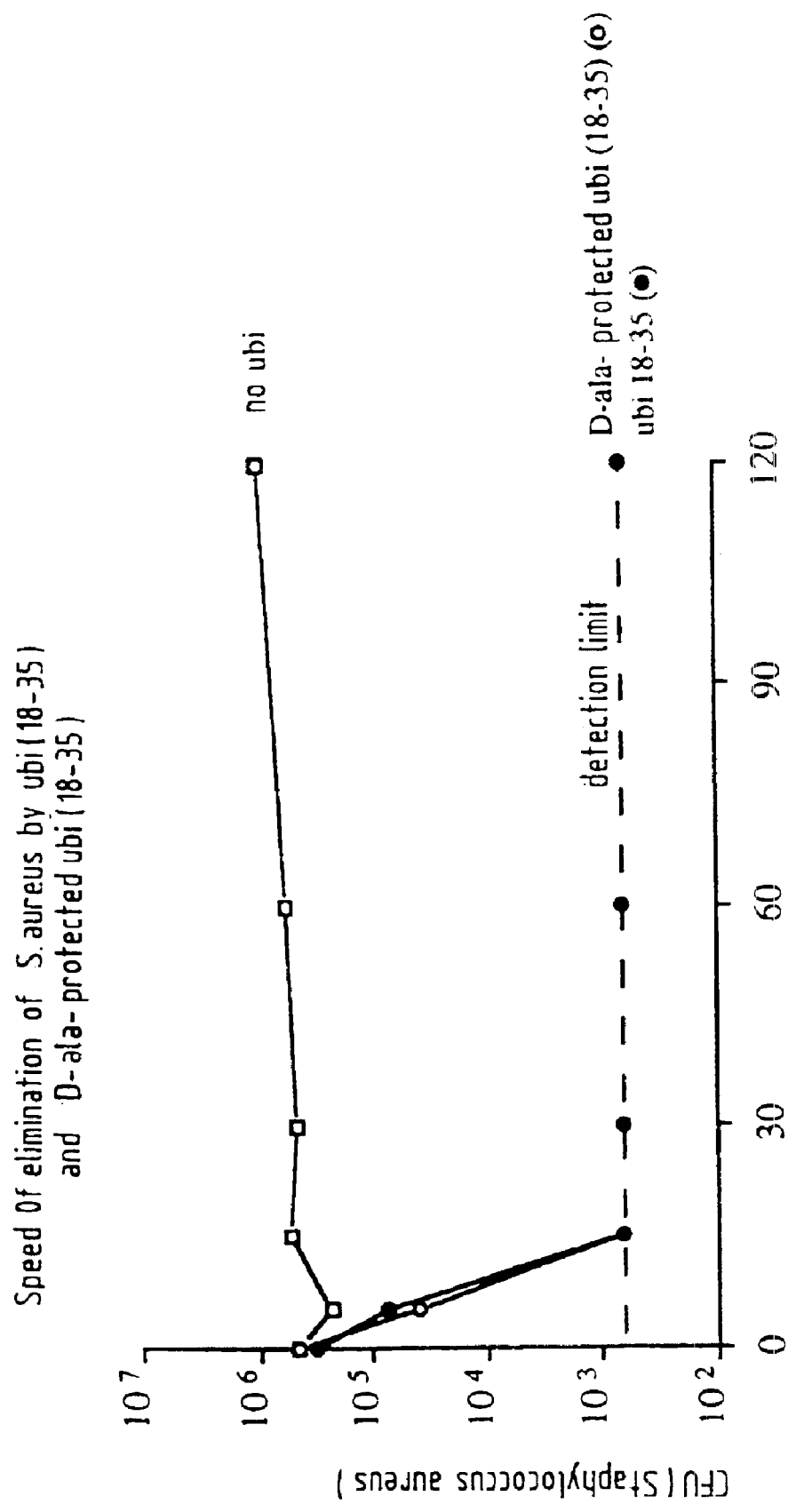
FIG. 7 shows the speed of ubiquicidine (18–35) and D-alanine-protected ubiquicidine (18–35) with which *Staphylococcus aureus* is eliminated

The maximum killing effect by both variants of ubiquicidine (ubiquicidine (18–35) and D-alanine-protected ubiquicidine (18–35)) on *Staphylococcus aureus* was achieved within 15 minutes (FIG. 7). The speed of elimination of *Staphylococcus aureus* bacteria by the two types of ubiquicidine peptide is identical (FIG. 7).

Figure 8:
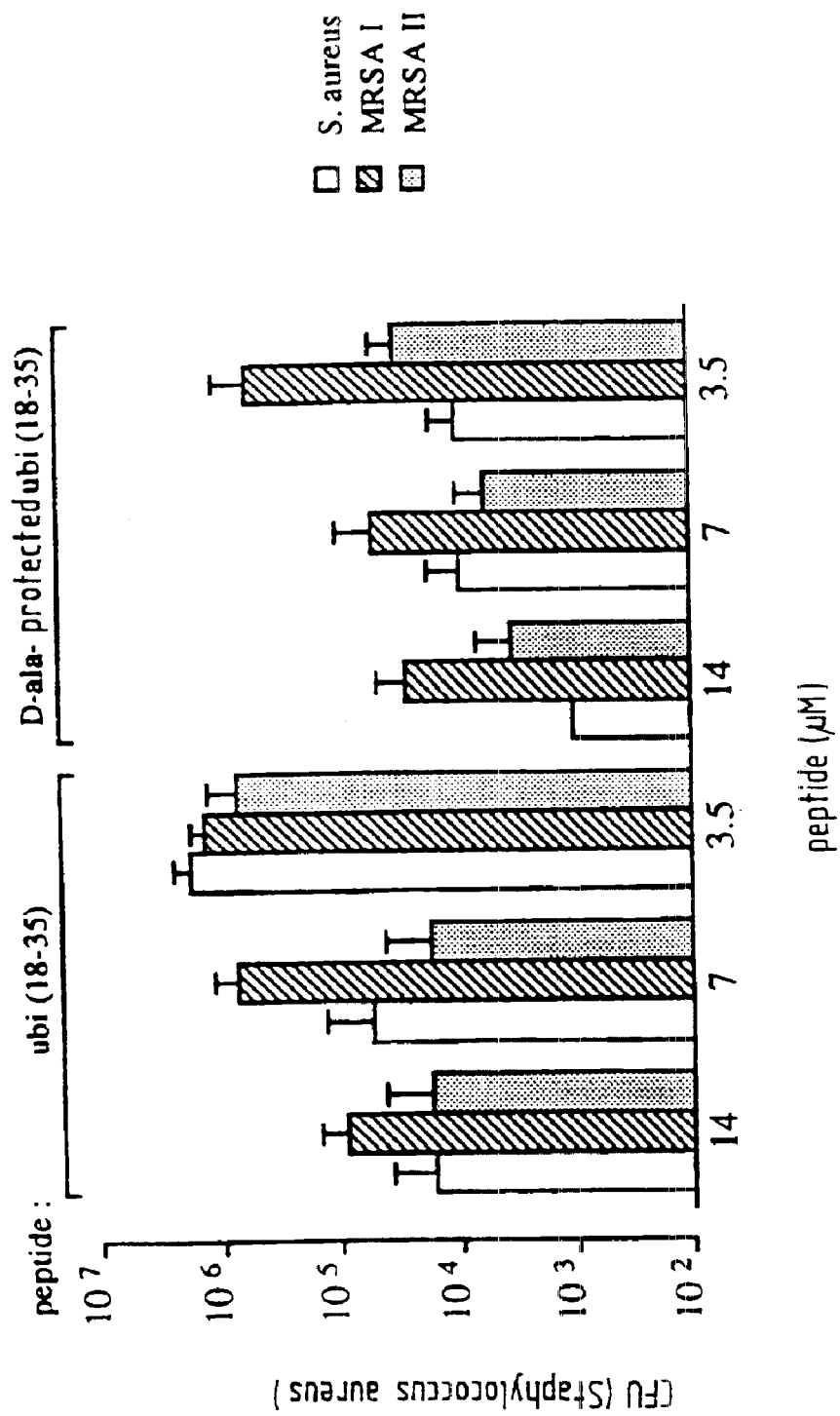
FIG. 8 shows the effect of ubiquicidine (18–35) and D-alanine-protected ubiquicidine (18–35) on (antibiotic-resistant) *Staphylococcus aureus*

The results further demonstrated that the D-alanine-protected ubiquicidine kills (multidrug resistant) *Staphylococcus aureus* more effectively than the unprotected variant (FIG. 8).

Figure 9:
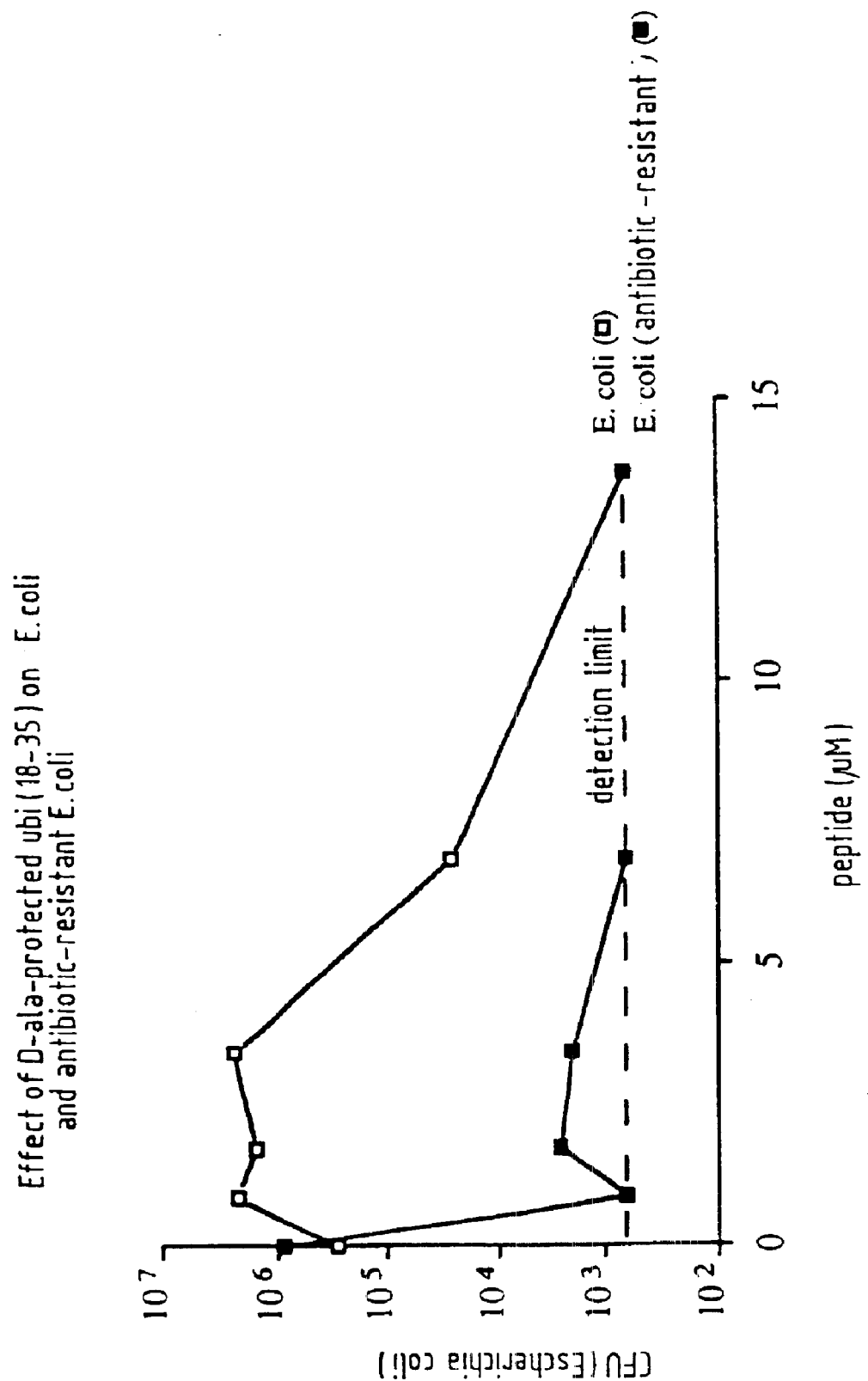
FIG. 9 shows the effect of D-alanine-protected ubiquicidine (18–35) on (antibiotic-resistant) *Escherichia coli*

Very surprising is the observation that the D-alanine-protected ubiquicidine (18–35) can kill antibiotic-resistant *Escherichia coli* much more effectively than the antibiotic-sensitive parent strain of *Escherichia coli* (FIG. 9). 1 $\mu$M D-alanine-protected ubiquicidine reduces the number of antibiotic-resistant bacteria to below the detection limit. A comparable antimicrobial effect relative to the parent strain is only achieved with 14 $\mu$M of the peptide. This data shows that antibiotic-resistant bacteria can be eliminated very effectively by peptides derived from ubiquicidine.

Example 4
Peptide Fragments Labelled with Technetium 99m

1. Introduction

A hybrid molecule was prepared by labelling the peptide fragments with the emitter $^{99m}$Tc. This example illustrates the manner of labelling according to the invention.

2. Materials and Method

Labelling of peptide D (ubiquicidine (18–35)), and the D-alanine-protected ubiquicidine (18–35) with $^{99m}$Tc was performed using a method according to the invention. For this purpose 10 $\mu$l of a MAG3-derived peptide solution (2 mg/ml in 0.01 M sodium phosphate pH 3.0) was added to 2 $\mu$l of a tin(II)pyrophosphate solution (0.5 mg/ml). Immediately thereafter 4 $\mu$l of a 10, mg/ml KBH$_4$ solution (Sigma Chemical Company, St. Louis, Mo., US) in 0.1 M NaOH was added. After adding 0.1 ml of a $^{99m}$Tc-sodium pertechnetate solution (20 MBq, Mallinckrodt Medical B.V., Petten, Netherlands) the mixture was stirred at room temperature for 30 minutes.

The radiochemical purity of peptides labelled with $^{99m}$Tc was determined after precipitation with 20% trichloroacetic acid (TCA), instantaneous thin-layer chromatography (ITLC) and HPLC. Summarizing, this took place by analysing 20 $\mu$l of a freshly prepared $^{99m}$Tc-defensin-1 or $^{99m}$Tc-IgG on a superose 12 column (Pharmacia, Upsala, Sweden), linked to an LKB Bromma HPLC 2249 chromatography pump (LKB, Upsala, Sweden) and an on-line NAI (Tl)-crystal-gamma-detection system (Raytest Steffi, Germany). The buffer which was used for analysing the $^{99m}$Tc-labelled compounds was 14 mM sodium phosphate-buffered salt solution (PBS) pH 7.5 with a flow rate of 1 ml/minute. Labelling yields of $^{99}$Tc-labelled peptides were determined after precipitation with 209 TCA, HPLC analysis and ITLC analysis and were respectively more than 90%, more than 90% and more than 95%.

Example 5
Accumulation of the Labelled Peptide at the Site of Infection
1. Introduction In order to demonstrate that the peptide (fragment) according to the invention is infection-seeking, the localization of $^{99}$Tc-labelled peptides (ubiquicidine (18–35), ubiquicidine (1–18) and defensins in addition to IgG as control) was determined using a γ-camera.

2. Materials and Method

Figure 10:
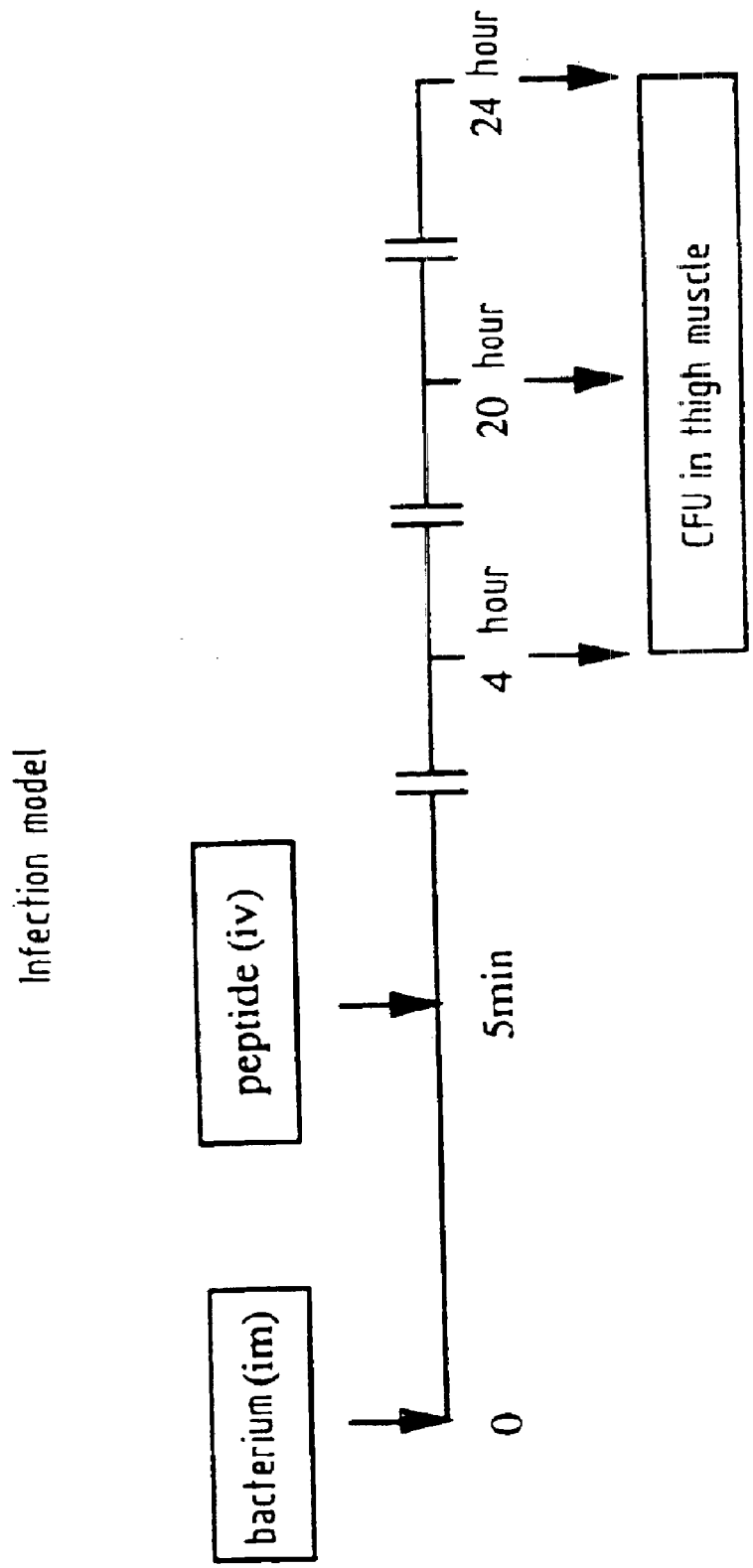
FIG. 10 is a scintigram of intraperitoneally administered $^{99m}$technetium-labelled ubiquicidine (18–35) in a mouse infected with *Staphylococcus aureus*

Mice were infected intramuscularly with about $10^6$ *Staphylococcus aureus* bacteria (ATCC 25923) and subsequently injected intraperitoneally with 25 μg $^{99m}$Tc-peptide. Mice were also injected intramuscularly with about $1 \times 10^8$ heat-killed (1 hour, 100° C.)*S. aureus*, 1 μg endotoxin or 100 ng phorbol myristate acetate (PMA) in order to cause sterile inflammations. At different points in time after injection of the peptide the radioactivity was measured in the circulation (heart), determined organs (liver, kidney, bladder and spleen) and in both thigh muscles using a γ-camera. Accumulation of the labelled peptide at the site of infection in the right thigh muscle is shown in FIG. 10.

3. Results

The results showed a very short half-life of the peptides in the circulation, i.e. $t_{half}$<15 minutes. The largest part of the injected labelled peptides (>60%) is removed via the liver, kidneys and bladder, but a part of the peptides (1–2% of the injected dose) arrives at the site of infection in the thigh muscle (FIG. 10).

Example 6
Antimicrobial Activity In Vivo
1. Introduction

The accumulation and antimicrobial activity in vivo of a number of ubiquicidine fragments was determined.

2. Materials and Methods
2.1. Infection Model

Figure 11:
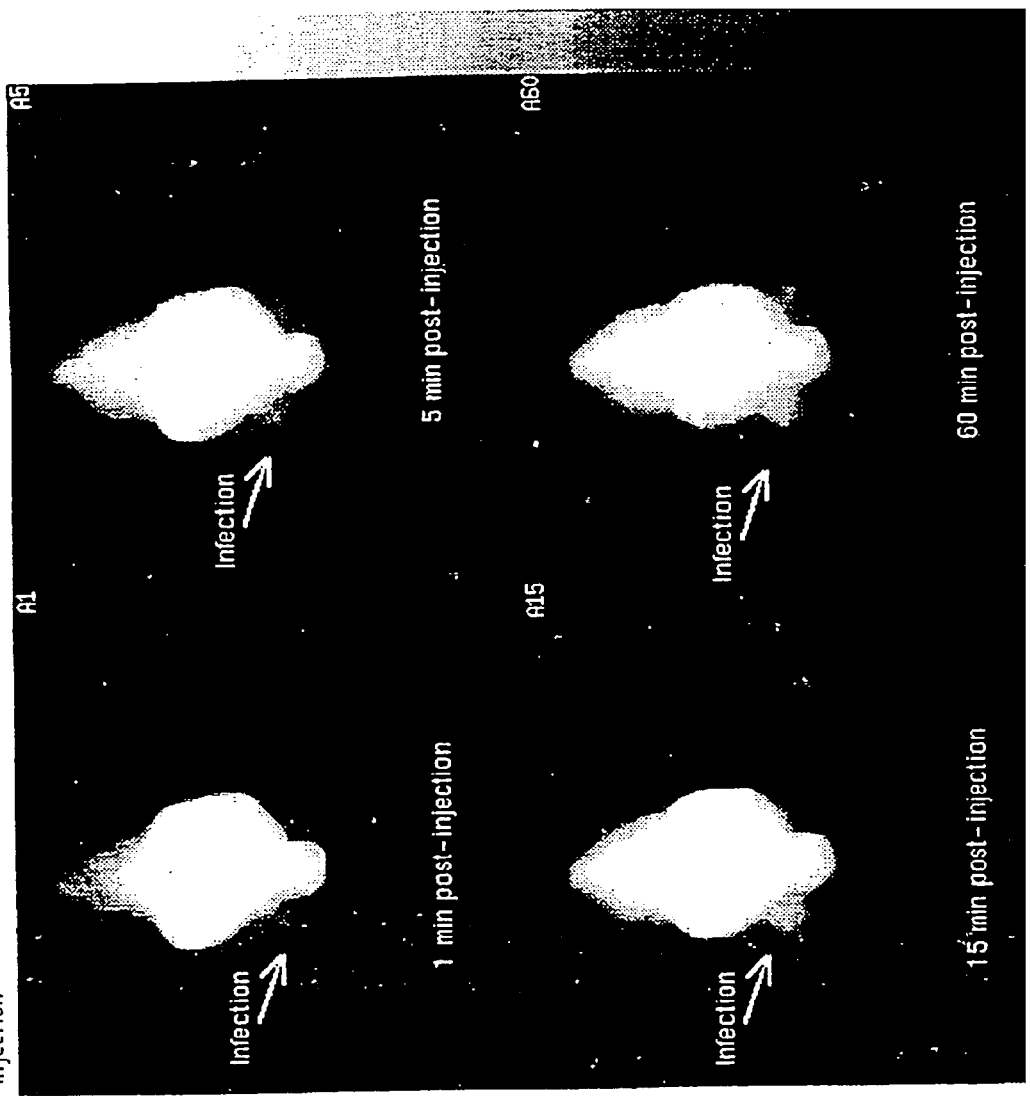
FIG. 11 is a schematic view of the experimental infection and treatment of mice

Reference is made to FIG. 11 for a schematic view of the experimental infection and treatment of the mice. In summary, mice-were infected intramuscularly in the right thigh muscle with about $10^6$ bacteria and after 5 minutes injected intraperitoneally with about 25 μg (labelled) peptide. At different points in time after injection of the peptide the animals were killed and the right thigh muscle was removed, homogenized, and finally the number of bacteria in the homogenate was determined using microbiological plate techniques, or accumulation of the labelled peptide was determined by means of a γ-camera. This test involved animals which were normal and immunocompromised (injection with cyclophosphamide, "total body" radiation).

2.2. Infection-seeking Effect of Peptides According to the Invention

Figure 12:
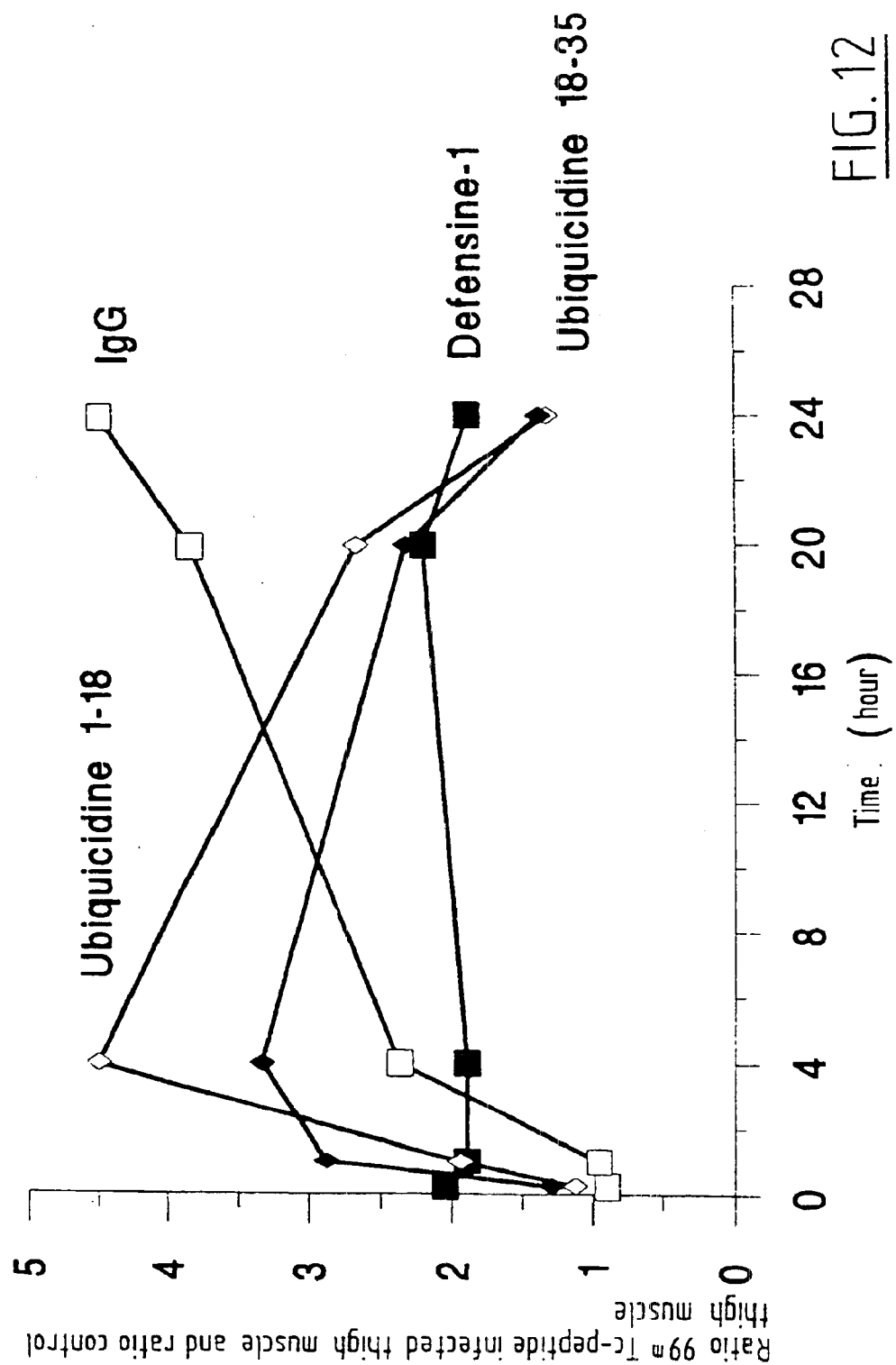
FIG. 12 shows the accumulation of $^{99m}$technetium-labelled ubiquicidine (18–35), ubiquicidine (1–18), defensins and human IgG in the thigh muscle infected with *Klebsiella pneumoninae*
Figure 13:
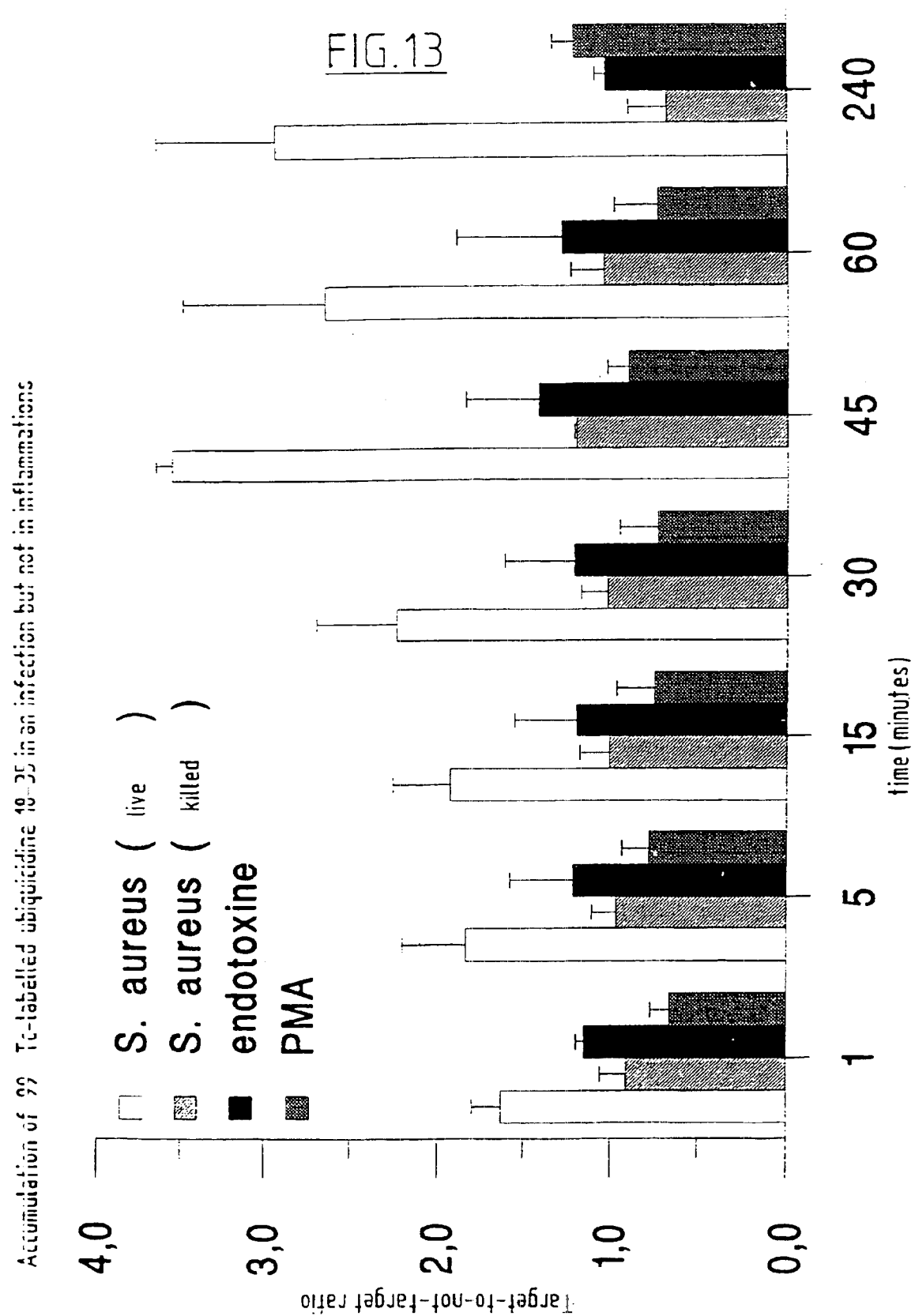
FIG. 13 shows the accumulation of 99mTc-labelled ubiquicidine 18–35 in a nidus but not in inflammations

Mice were infected in the right thigh muscle with *Klebsiella pneumoniae* and 25 μg $^{99m}$Tc-labelled ubiquicidine (1–18) or ubiquicidine (18–35) was subsequently injected intraperitoneally. At different points in time after injection of the peptide the amount of activity in the right (test) and left (control) thigh muscle of the mouse was measured using a γ-camera. The results are shown in FIG. 12 as a ratio of the values in the right thigh muscle and the left thigh muscle, i.e. "target to non-target ratio". For the purpose of comparison the results for human defensin and IgG are also shown. The target to non-target ratios for infections and sterile inflammations were also compared (FIG. 13).

2.3. Effect of Antimicrobial Peptides on Experimental Infections

Mice were infected in the right thigh muscle with *Klebsiella pneumoniae* (A) or *Staphylococcus aureus* (B). 5 minutes later, 25 μg ubiquicidine (18–35) or ubiquicidine (1–18) was injected intraperitoneally. 24 hours after administering of the peptide the animals were killed and the number of bacteria in the right thigh muscle was quantified microbiologically. As positive control, animals were injected intraperitoneally with human defensin and as negative control with the solvent of the antimicrobial peptides. The result is shown in FIG. 14. The mice were also injected with 150 mg cyclophosphamide/kg body weight. Four days afterwards the animals were infected in the right thigh muscle with *K. pneumonia* and a day later different quantities of ubiquicidine (18–35), ubiquicidine (29–41) or defensin-1 were injected intravenously. Twenty-four hours after administering of the peptide the animals were killed and the number of bacteria in the right thigh muscle was quantified microbiologically. As control, normal animals were treated in identical manner. The result is shown in FIG. 15.

3. Results

The accumulation of the tested peptides was found to be maximal 4 hours after administration and subsequently decreases in the course of time (FIG. 12). It is notable that the maximum accumulation of $^{99}$Tc-ubiquicidine (1–18) and $^{99}$Tc-ubiquicidine (18–35) is reached much sooner than $^{99}$Tc-IgG. This observation implies that $^{99}$Tc-ubiquicidine peptides can be of importance for faster diagnostics of infections. Comparable results were found when the $^{99}$Tc-peptide was administered intravenously 24 hours after infection.

The above stated pharmacological data shows that ubiquicidine (1–18) and ubiquicidine (18–35) accumulate rapidly in the infected thigh muscle. The results of our experiments into the effect of these peptides on the number of bacteria in the muscle demonstrate that ubiquicidine (18–35) eliminates bacteria more effectively than ubiquicidine (1–18) and defensins (FIG. 12). These in vivo results correspond very well with the results of the in vitro experiments.

FIG. 14 shows that particularly ubiquicidine (18–35) also has a marked bactericidal effect in vivo which is better than that of defensin.

The result in immunocompromised animals (FIG. 15) shows that the bactericidal effect in vivo is determined by a direct bactericidal effect as well as by an immunomodulating effect.

What is claimed is:

1. Peptide fragment derived from ubiquicidine having antimicrobial activity and comprising a continuous series of between 6 to 18 amino acids from the amino acid sequence of ubiquicidine:
KVHGSLARAGKVRGQTPKVAKQEKKKKK-TGRAKRRMQYNRRFVNVVPTFGKKKGPN ANS, (SEQ ID NO: 1) which does not include peptides having the amino acid sequence KVHGSLARAGKVRGQTPKVAKQ (SEQ ID NO: 10) or AGKVRGQTPKVAKQEKKKKKT (SEQ ID NO: 11).

2. Peptide fragment as claimed in claim 1, comprising a continuous series of between 6 to 18 amino acids from the amino acid sequence of ubiquicidine:
KVHGSLARAGKVRGQTPKVAKQEKKKKK-TGRAKRRMQYNRRFVNVVPTFGKKKGPN ANS, (SEQ ID NO: 1) which does not include peptides having the amino acid sequence KVHGSLARAGKVRGQTPKVAKQ (SEQ ID NO: 10) or AGKVRGQTPKVAKQEKKKKKT (SEQ ID NO: 11).

3. Peptide fragment as claimed in claim 1, consisting of the following amino acid sequences:

| | |
|---|---|
| ubiquicidine (1–18) | KVHGSLARAGKVRGQTPK (SEQ ID NO: 2) |
| ubiquicidine (29–41) | TGRAKRRMQYNRR (SEQ ID NO: 3) |
| ubiquicidine (18–29) | KVAKQEKKKKKT (SEQ ID NO: 4) |
| ubiquicidine (18–35) | KVAKQEKKKKKTGRAKRR (SEQ ID NO: 5) |
| ubiquicidine (29–35) | TGRAKRR (SEQ ID NO: 7) |
| ubiquicidine (42–59) | FVNVVPTFGKKKGPNANS (SEQ ID NO: 8) |
| ubiquicidine (36–41) | MQYNRR (SEQ ID NO: 9). |

4. Derivative of ubiquicidine or of a peptide fragment derived from ubiquicidine having antimicrobial activity and comprising a continuous series of between 6 to 18 amino acids from the amino acid sequence of ubiquicidine:
KVHGSLARAGKVRGQTPKVAKQEKKKKK-TGRAKRRMQYNRRFVNVVPTFGKKKGPNA NS, (SEQ ID NO: 1) which derivative has an amino acid sequence which is at least partly the reverse of the amino acid sequence of the corresponding original peptide.

5. Derivative of a ubiquicidine or of a peptide fragment derived from ubiquicidine having antimicrobial activity and comprising a continuous series of between 6 to 18 amino acids from the amino acid sequence of ubiquicidine:
KVHGSLARAGKVRGQTPKVAKQEKKKKK-TGRAKRRMQYNRRFVNVVPTFGKKKGPNA NS, (SEQ ID NO: 1) wherein at least one of the amino acids from the original peptide is replaced by a stereoisomer of that amino acid.

6. Derivative of ubiquicidine or of a peptide fragment derived from ubiquicidine having antimicrobial activity and comprising a continuous series of between 6 to 18 amino acids from the amino acid sequence of ubiquicidine:
KVHGSLARAGKVRGQTPKVAKQEKKKKK-TGRAKRRMQYNRRFVNVVPTFGKKKGPNA NS, (SEQ ID NO: 1) wherein the original amino acid chain is extended at one or both ends thereof with one or more groups, such as D-amino acids, protecting against degradation.

7. Derivative as claimed in claim 6, wherein the original amino acid chain is extended at one or both ends thereof with one or more groups of D-alanine.

8. A method for the therapy of an infection in humans and animals, comprising:
a) administering an antimicrobial compound having antimicrobial activity selected from the group consisting of ubiquicidine, a derivative of ubiquicidine, and a peptide fragment derived from ubiquicidine and comprising a continuous series of between 6 to 18 amino acids from the amino acid sequence of ubiquicidine:
KVHGSLARAGKVRGQTPKVAKQEKKKKK-TGRAKRRMQYNRRFVNVVP TFGKKKGPNANS (SEQ ID NO: 1); and
b) treating the infection, wherein the antimicrobial action of the compound results in inhibiting or otherwise exerting a negative effect on the infection.

9. The method of claim 8, wherein the peptide fragment comprises a peptide fragment, comprising a continuous series of between 6 to 18 amino acids from the amino acid sequence of ubiquicidine:
KVHGSLARAGKVRGQTPKVAKQEKKKKK-TGRAKRRMQYNRRFVNVVPTFGKKKGPN ANS, (SEQ ID NO: 1) with the exception of peptides having the amino acid sequence KVHGSLARAGKVRGQTP-KVAKQ (SEQ ID NO: 10) or AGKVRGQTPK-VAKQEKKKKKT (SEQ ID NO: 11).

10. The method of claim 8, wherein the derivative comprises a derivative of ubiquicidine or of a peptide fragment derived from ubiquicidine and comprising a continuous series of between 6 to 18 amino acids from the amino acid sequence of ubiquicidine:
KVHGSLARAGKVRGQTPKVAKQEKKKKK-TGRAKRRMQYNRRFVNVVPTFGKKKGPN ANS, (SEQ ID NO: 1) which derivative has an amino acid sequence which is at least partly the reverse of the amino acid sequence of the corresponding original peptide.

11. The method of claim 8, wherein the microbial infection is caused by a microorganism selected from the group consisting of Gram-positive bacteria, Gram-negative bacteria, fungi and viruses.

12. Antimicrobial agent, comprising at least a suitable quantity of one or more active components chosen from ubiquicidine and/or peptide fragments derived from ubiquicidine, said ubiquicidine and/or said peptide fragments derived from ubiquicidine having antimicrobial activity, and comprising a continuous series of between 6 to 18 amino acids from the amino acid sequence of ubiquicidine:

KVHGSLARAGKVRGQTPKVAKQEKKKKK-TGRAKRRMQYNRRFVNVVPTFGKKKGPN ANS (SEQ ID NO: 1).

13. The method of claim 8, wherein the compound comprises an antimicrobial agent, comprising at least a suitable quantity of one or more active components chosen from ubiquicidine, peptide fragments derived from ubiquicidine and comprising a continuous series of between 6 to 18 amino acids from the amino acid sequence of ubiquicidine:

KVHGSLARAGKVRGQTPKVAKQEKKKKK-TGRAKRRMQYNRRFVNVVPTFGKKKGPN ANS (SEQ ID NO: 1).

14. Method for monitoring a treatment, comprising:

a) administering an antimicrobial agent having antimicrobial activity, comprising at least a suitable quantity of one or more active components chosen from ubiquicidine, peptide fragments derived from ubiquicidine and comprising a continuous series of between 6 to 18 amino acids from the amino acid sequence of ubiquicidine:

KVHGSLARAGKVRGQTPKVAKQEKKKKK-TGRAKRRMQYNRRFVNVVP TFGKKKGPNANS (SEQ ID NO: 1), b) observing the localization of the agent in time, and c) following the effect of the treatment, wherein the antimicrobial action of the compound results in inhibiting or otherwise exerting a negative effect on the infection.

15. Antimicrobial agent as claimed in claim 12, further comprising at least one excipient.

16. Method for providing prophylactic action against an infection in humans or animals, comprising:

a) administering a peptide fragment, derived from ubiquicidine having antimicrobial activity and comprising a continuous series of between 6 to 18 amino acids from the amino acid sequence of ubiquicidine:

KVHGSLARAGKVRGQTPKVAKQEKKKKK-TGRAKRRMQYNRRFVNVVP TFGKKKGPNANS, (SEQ ID NO: 1) which does not include peptides having the amino acid sequence KVHGSLARAGKVRGQTPKVAKQ (SEQ ID NO: 10) or AGKVRGQTPKVAKQEKKKKKT (SEQ ID NO: 11) in the form of a coating, wherein said administration results in preventing the infection.

* * * * *

UNITED STATES PATENT AND TRADEMARK OFFICE
CERTIFICATE OF CORRECTION

PATENT NO.     : 6,884,776 B1
DATED          : April 26, 2005
INVENTOR(S)    : Nibbering et al.

It is certified that error appears in the above-identified patent and that said Letters Patent is hereby corrected as shown below:

Title page,
Item [22], PCT Filed: "May 18, 1998" should read -- May 29, 1998 --.
Item [56], References Cited, FOREIGN PATENT DOCUMENTS, add the following:
-- WIPO     9116076     10/1991 --;
OTHER PUBLICATIONS, "Hiemstra" reference, "Murise" should read -- Murine --;
"Pauwels" reference, "...LDL wish", Tc:" should read -- ...LDL with $^{99m}$Tc: --;
"Pauwels" reference, "Stammous Chlorida" should read -- Stannous Chloride --; and
"Martin, Edith" reference, "esdogenous" should read -- endogenous --.

Signed and Sealed this

Eleventh Day of October, 2005

JON W. DUDAS
*Director of the United States Patent and Trademark Office*

SEQUENCE LISTING

<160> NUMBER OF SEQ ID NOS: 11

<210> SEQ ID NO 1
<211> LENGTH: 59
<212> TYPE: PRT
<213> ORGANISM: Unknown Organism
<220> FEATURE:
<223> OTHER INFORMATION: Description of Unknown Organism: Mammalian -continued

<400> SEQUENCE: 1

Lys Val His Gly Ser Leu Ala Arg Ala Gly Lys Val Arg Gly Gln Thr
 1               5                  10                  15
Pro Lys Val Ala Lys Gln Glu Lys Lys Lys Lys Thr Gly Arg Ala
            20                  25                  30
Lys Arg Met Gln Tyr Asn Arg Arg Phe Val Asn Val Val Pro Thr
        35                  40                  45
Phe Gly Lys Lys Lys Gly Pro Asn Ala Asn Ser
    50                  55

<210> SEQ ID NO 2
<211> LENGTH: 18
<212> TYPE: PRT
<213> ORGANISM: Artificial Sequence
<220> FEATURE:
<223> OTHER INFORMATION: Description of Artificial Sequence: peptide
      1-18

<400> SEQUENCE: 2

Lys Val His Gly Ser Leu Ala Arg Ala Gly Lys Val Arg Gly Gln Thr
 1               5                  10                  15
Pro Lys
    18

<210> SEQ ID NO 3
<211> LENGTH: 13
<212> TYPE: PRT
<213> ORGANISM: Artificial Sequence
<220> FEATURE:
<223> OTHER INFORMATION: Description of Artificial Sequence: peptide
      29-41

<400> SEQUENCE: 3

Thr Gly Arg Ala Lys Arg Arg Met Gln Tyr Asn Arg Arg
 1               5                  10

<210> SEQ ID NO 4
<211> LENGTH: 12
<212> TYPE: PRT
<213> ORGANISM: Artificial Sequence
<220> FEATURE:
<223> OTHER INFORMATION: Description of Artificial Sequence: peptide
      18-29

<400> SEQUENCE: 4

Lys Val Ala Lys Gln Glu Lys Lys Lys Lys Thr
 1               5                  10

<210> SEQ ID NO 5
<211> LENGTH: 18
<212> TYPE: PRT
<213> ORGANISM: Artificial Sequence
<220> FEATURE:
<223> OTHER INFORMATION: Description of Artificial Sequence: peptide
      18-35

<400> SEQUENCE: 5

Lys Val Ala Lys Gln Glu Lys Lys Lys Lys Thr Gly Arg Ala Lys
 1               5                  10                  15
Arg Arg
    18

```
<210> SEQ ID NO 6
<211> LENGTH: 20
<212> TYPE: PRT
<213> ORGANISM: Artificial Sequence
<220> FEATURE:
<223> OTHER INFORMATION: Description of Artificial Sequence: peptide
      18-35 with D-alanine on both ends

<400> SEQUENCE: 6

Ala Lys Val Ala Lys Gln Glu Lys Lys Lys Lys Thr Gly Arg Ala
 1               5                  10                  15

Lys Arg Arg Ala
            20

<210> SEQ ID NO 7
<211> LENGTH: 7
<212> TYPE: PRT
<213> ORGANISM: Artificial Sequence
<220> FEATURE:
<223> OTHER INFORMATION: Description of Artificial Sequence: peptide
      29-35

<400> SEQUENCE: 7

Thr Gly Arg Ala Lys Arg Arg
 1               5

<210> SEQ ID NO 8
<211> LENGTH: 18
<212> TYPE: PRT
<213> ORGANISM: Artificial Sequence
<220> FEATURE:
<223> OTHER INFORMATION: Description of Artificial Sequence: peptide
      42-59

<400> SEQUENCE: 8

Phe Val Asn Val Val Pro Thr Phe Gly Lys Lys Lys Gly Pro Asn Ala
 1               5                  10                  15

Asn Ser
     18

<210> SEQ ID NO 9
<211> LENGTH: 6
<212> TYPE: PRT
<213> ORGANISM: Artificial Sequence
<220> FEATURE:
<223> OTHER INFORMATION: Description of Artificial Sequence: peptide
      36-41

<400> SEQUENCE: 9

Met Gln Tyr Asn Arg Arg
 1               5

<210> SEQ ID NO 10
<211> LENGTH: 22
<212> TYPE: PRT
<213> ORGANISM: Artificial Sequence
<220> FEATURE:
<223> OTHER INFORMATION: Description of Artificial Sequence: peptide
      1-22

<400> SEQUENCE: 10

Lys Val His Gly Ser Leu Ala Arg Ala Gly Lys Val Arg Gly Gln Thr
 1               5                  10                  15

Pro Lys Val Ala Lys Gln
            20
```

```
<210> SEQ ID NO 11
<211> LENGTH: 21
<212> TYPE: PRT
<213> ORGANISM: Artificial Sequence
<220> FEATURE:
<223> OTHER INFORMATION: Description of Artificial Sequence: peptide
      9-29

<400> SEQUENCE: 11

Ala Gly Lys Val Arg Gly Gln Thr Pro Lys Val Ala Lys Gln Glu Lys
 1               5                  10                  15

Lys Lys Lys Lys Thr
            20
```